United States Patent
Maiti et al.

(10) Patent No.: US 10,662,445 B2
(45) Date of Patent: May 26, 2020

(54) PROCESS FOR THE PRODUCTION OF BIO-BUTANOL BY FERMENTATION OF GLYCOSIDIC WASTE MATTER

(71) Applicants: INSTITUT NATIONAL DE LA RECHERCHE SCIENTIFIQUE—CENTRE EAU TERRE ENVIRONNEMENT, Quebec (CA); CENTRE DE RECHERCHE INDUSTRIELLE DU QUEBEC, Quebec (CA)

(72) Inventors: Sampa Maiti, West Bengal (IN); Satinder Kaur Brar, Quebec (CA); Yann LeBihan, Quebec (CA); Gorka Gallastegui Ruiz de Gordoa, Vitoria-Gasteiz (ES)

(73) Assignees: INSTITUT NATIONAL DE LA RECHERCHE SCIENTIFIQUE, Quebec (CA); CENTRE DE RECHERCHE INDUSTRIELLE DU QUEBEC, Quebec (CA)

( * ) Notice: Subject to any disclaimer, the term of this patent is extended or adjusted under 35 U.S.C. 154(b) by 127 days.

(21) Appl. No.: 16/058,540

(22) Filed: Aug. 8, 2018

(65) Prior Publication Data
US 2020/0048661 A1 Feb. 13, 2020

(51) Int. Cl.
*C12P 7/16* (2006.01)
*B01D 11/04* (2006.01)
*B01D 11/02* (2006.01)

(52) U.S. Cl.
CPC ............ *C12P 7/16* (2013.01); *B01D 11/0288* (2013.01); *B01D 11/0492* (2013.01); *C12P 2203/00* (2013.01)

(58) Field of Classification Search
CPC ...................................................... C12P 7/16
USPC ......................................................... 435/160
See application file for complete search history.

(56) References Cited

PUBLICATIONS

Maiti et al. Chemical Engineering Journal, 2017, vol. 330, pp. 1100-1108 (Year: 2017).*
Piotrowski et al. "Death by a thousand cuts: the challenges and diverse landscape of lignocellulosic hydrolysate inhibitors", Frontiers in Microbiology, vol. 5, 2014: 90, 1-8.
Martinez et al. "Detoxification of dilute acid hydrolysates of lignocellulose with lime", Biotechnology progress, vol. 17(2), 2001: 287-293.
Ge et al. "Comparison of different detoxification methods for corn cob hemiceluose hydrolysate to improve ethanol production by Candida shehatae ACCC 20335". African Journal of Microbiology Research, vol. 5(10), 2011: 1163-1168.
Miller "Use of dinitrosalicylic acid reagent for determination of reducing sugar", Analytical chemistry, vol. 31(3), 1959: 426-428.
Ranjan et al. "Biobutanol: science, engineering, and economics", International Journal of Energy Research, vol. 36(3), 2012: 277-323.
Ujor et al. "Glycerol supplementation of the growth medium enhances in situ detoxification of furfural by Clostridium beijerinckii during butanol fermentation", Applied microbiology and biotechnology, vol. 98(14), 2014: 6511-6521.
Palmqvist et al. "Fermentation of lignocellulosic hydrolysates. II: inhibitors and mechanisms of inhibition", Bioresource technology, vol. 74(1), 2000: 25-33.
Qureshi et al. "Effect of cellulosic sugar degradation products (furfural and hydroxymethyl furfural) on acetone-butanol—ethanol (ABE) fermentation using Clostridium beijerinckii P260", Food and Bioproducts Processing, vol. 90(3), 2012: 533-540.
Zhang et al. "Biotransformation of furfural and 5-hydroxymethyl furfural (HMF) by Clostridium acetobutylicum ATCC 824 during butanol fermentation", New Biotechnology, vol. 1(3), 2012: 345-351.
Ramos et al. "Mechanisms of solvent tolerance in gram-negative bacteria", Annual Reviews in Microbiology, vol. 56(1), 2002: 743-768.
Jönsson et al. "Bioconversion of lignocellulose: inhibitors and detoxification", Biotechnology for biofuels, vol. 6(1), 2013, 1-10.
López-Linares et al. "Hemicellulose-derived sugars solubilisation of rape straw. Cofermentation of pentoses and hexoses by *Escherichia coli*", Spanish Journal of Agricultural Research, vol. 13(3), 2015: 213, 1-10.
Gupta et al. "Scale-up of abatement of fermentation inhibitors from acid hydrolysates for efficient conversion to ethanol as biofuel", Journal of Chemical Technology and Biotechnology, vol. 91(6), 2016: 1826-1834.
Ascon-Cabrera et al. "Interfacial area effects of a biphasic aqueous/organic system on growth kinetic of xenobiotic-degrading microorganisms" Applied microbiology and biotechnology, vol. 43(6), 1995: 1136-1141.
Gardin et al. "Biodegradation of xylene and butyl acetate using an aqueous-silicon oil two-phase system", Biodegradation, vol. 0(3), 1999: 193-200.
Kraemer et al. "Separation of butanol from acetone-butanol-ethanol fermentation by a hybrid extraction-distillation process", Computers & Chemical Engineering, vol. 35(5), 2011: 949-963.

(Continued)

*Primary Examiner* — Tekchand Saidha
(74) *Attorney, Agent, or Firm* — Benoit & Cote, Inc.; Philip L. Conrad; Mathieu Miron

(57) ABSTRACT

An efficient, rapid ex-situ detoxification has been developed to reduce inhibitor concentration and enhance acetone-butanol-ethanol (ABE) production from brewery industry liquid waste (BLW) and brewery spent grain (BSG). About 80±2.0% extraction of furan derivative and more than 95±2.0% extraction of phenolic compounds and almost no extraction of reducing sugar from simulated synthetic media as well as real waste hydrolysate have been obtained. Ex-situ extraction of microbial inhibitors from BLW and BSG hydrolysates using bis-(2-ethylhexyl) sebacate as solvent leads to high production of ABE of 12.67 g/L and 11.23 g/L respectively. Lower power consumption (0.081 W/L) and reuse of the extracting solvent made this detoxification technique extremely useful for improving production of bio-butanol from agro-industrial waste.

20 Claims, 3 Drawing Sheets

(56) References Cited

PUBLICATIONS

Morone et al. "Levulinic acid production from renewable waste resources: bottlenecks, potential remedies, advancements and applications", Renewable and Sustainable Energy Reviews, vol. 51, 2015: 548-565.

Tarabanko et al. "Sodium hydrosulfate as the catalyst for carbohydrate conversion into the levulinic acid and 5-hydroxymetylfurfural derivatives", Journal of Siberian Federal University, vol. 1, 2008: 35-49.

Hu et al. "One-pot synthesis of levulinic acid/ester from C5 carbohydrates in a methanol medium", ACS Sustainable Chemistry Engineering, vol. 1, 2013: 1593-1599.

Tomei et al., "Two-phase reactors applied to the removal of substituted phenols: comparision between liquid-liquid and solid-liquid systems", Water Science and Technology, Aug. 2010, vol. 62, pp. 776-782.

Hu et al. "Pretreatment and lignocellulosic chemistry", Bioenergy Research, vol. 5(4), 2012: 1043-1066.

Cascone: "Biobutanol: A Replacement for Bioethanol?", Chemical Engineering Progress, vol. 104(8), 2008.

Papoutsakis "Engineering solventogenic clostridia", Current opinion in biotechnology, vol. 19(5), 2008: 420-429.

Qureshi et al. "Economics of butanol fermentation using hyperbutanol producing Clostridium beijerinckii BA101", Food and bioproducts processing, vol. 78(3), 2000: 139-144.

Tao et al. "Comparative techno-economic analysis and reviews of n-butanol production from corn grain and corn stover", Biofuels, Bioproducts and Biorefining, vol. 8(3), 2014: 342-361.

Maiti et al. "Agro-industrial wastes as feedstock for sustainable bio-production of butanol by Clostridium beijerinckii", Food and Bioproducts Processing, vol. 98, Jan. 11, 2016: 217-226.

Lin et al. Food waste as a valuable resource for the production of chemicals, materials and fuels. Current situation and global perspective. Energy Environmental Sci., vol. 6(2), 2013: 426-464.

Dhillon et al. "Utilization of different agro-industrial wastes for sustainable bioproduction of citric acid by Aspergillus niger", Biochemical Engineering Journal, 83-92.

Dhillon et al. "Perspective of apple processing wastes as low-cost substrates for bioproduction of high value products: A review", Renewable and Sustainable Energy Reviews 27, 789-805.

Dhillon et al. "Enhanced solid-state citric acid bio-production using appled pomace waste through surface response methodology", Journal of Applied Microbiology, vol. 110, 2011: 1045-1055.

Fillaudeau et al. "Water, wastewater and waste management in brewing industries", Journal of Cleaner Production, vol. 14(5), 2006, 463-471.

Olajire "The brewing industry and environmental challenges", Journal of cleaner production, vol. 30, 2012, 1-21.

Mielcarek et al. "Biodegradability evaluation of wastewaters from malt and beer production". Journal of the Institute of Brewing, vol. 119(4), 2013: 242-250.

Mussatto et al. "Techno-economic analysis for brewer's spent grains use on a biorefinery concept: The Brazilian case", Bioresource technology, vol. 148, 2013: 302-310.

Global Methane Initiative. (2011) "Resource assessment for livestock and agro-industrial wastes—India".

Gassara et al. "Pomace waste management scenarios in Québec—impact on greenhouse gas emissions", Journal of hazardous materials, vol. 192(3), 2011: 1178-1185.

Ezeji et al. "Bioproduction of butanol from biomass: from genes to bioreactors", Current opinion in biotechnology, vol. 18(3), 2007: 220-227.

Gürbüz et al. "Conversion of hemicellulose to furfural and levulinic acid using biphasic reactors with alkylphenol solvents" ChemSusChem, vol. 5(2), 2012: 383-387.

Jönsson et al. "Bioconversion of lignocellulose: inhibitors and detoxification", Biotechnology for biofuels, vol. 6, Issue 1, 2013: 1-10.

Szabolcs et al. "Microwave-assisted conversion of carbohydrates to levulinic acid: an essential step in biomass conversion" Green Chemistry, vol. 15, 2013, 439-445.

Macheiner et al. "Pretreatment and hydrolysis of brewer's spent grains", Engineering in life sciences, vol. 3(10), 2003: 401-405.

\* cited by examiner

PROCESS FOR THE PRODUCTION OF BIO-BUTANOL BY FERMENTATION OF GLYCOSIDIC WASTE MATTER

BACKGROUND

(a) Field

The subject matter disclosed relates to processes for the extraction of microbial inhibitors from hydrolyzed glycosidic waste matter containing free reducing sugars and for the production of bio-butanol from fermentation of detoxified hydrolyzed glycosidic waste matter containing free reducing sugars obtained therefrom. Detoxification is achieved by solvent extraction of the hydrolyzed glycosidic waste matter containing free reducing sugars with a solvent selected from the group consisting of bis-(2-ethylhexyl) sebacate, 2-undecanone, or a combination thereof.

(b) Related Prior Art

Continuous global energy demand and concern over increasingly expensive imported oil and diesel resources has led to the development of renewable energy sources that have driven research towards the utilization of lignocellulosic food- and agro-industrial wastes as feedstock for the production of biofuels Thus, establishment of vigorous bio-based industry capable of producing bio-fuel is compulsory to supplement petroleum as the main feedstock for fuel. However, as the demand for food resources increases, the search for renewable nonfood resources to displace substantial amounts of nonrenewable fossil fuels rests largely on low-cost lignocellulosics (Hu et al. Pretreatment and lignocellulosic chemistry. Bioenergy Research, Vol. 5(4), 2012: 1043-1066).

Bio-butanol, four carbons containing aliphatic alcohol has been recently considered as one of the emerging second generation liquid biofuel (Maiti et al., Agro-industrial wastes as feedstock for sustainable bio-production of butanol by *Clostridium beijerinckii*. Food and Bioproducts Processing, 98, 217-226). Butanol is considered as a superior bio-fuel due to its higher energy density (29.2 MJ/L), higher air fuel ratio (11.2), octane number (96), lower heat of evaporation (0.43 MJ/kg), and its ability to blend with gasoline in higher percentage (80-85%) without any modification of conventional Otto-cycle engine compared to bioethanol, which has energy density (19.6 MJ/L), higher air fuel ratio (9), octane number (126) and lower heat of evaporation (0.92 MJ/kg). As a liquid transportation fuel, butanol is superior to the first generation biofuel due to higher energy content, since butanol releases 96% of the energy of a gasoline volume unit, whereas ethanol only generates 73% of gasoline energy per unit volume and other properties such as low volatility, higher blending rate with gasoline without engine modification, decrease emission of $NO_x$, octane improving power, convenient distribution using current pipeline infrastructure, and better auto-emission performance (Cascone. Biobutanol: A Replacement for Bioethanol?. Chemical Engineering Progress, Vol. 104(8), 2008; Maiti et al., March 2016).

Bio-butanol has been produced by anaerobic ABE (acetone-butanol-ethanol) fermentation of different raw materials such as, monosaccharides (e.g. glucose, xylose etc.), poly-saccharides (e.g. starch), complex biomass (e.g. lignocellulose) etc., using solventogenic Clostridia strains (Papoutsakis. Engineering solventogenic clostridia. Current opinion in biotechnology, Vol. 19(5), 2008: 420-429). Techno-economic bio-butanol production evaluation showed that low cost substrates are required since the raw feedstock cost is the largest cost contributor to the total operating cost (60-70%). In an attempt to reduce the cost of butanol production by fermentation, the use of a variety of low cost feedstocks have been investigated including soy molasses, cracked corn, starch based packing peanuts, maltodextrin, and various other agricultural biomass products. Novel agricultural substrates used for the production of biofuels include wood (hardwood), by-products left over from the corn milling processes (corn fiber), residues from annual plants, whey permeate, and waste paper. While agricultural residues such as straws (wheat and rice) and corn fiber are economically available, these materials must first be subjected to pretreatment and enzymatic hydrolysis to produce hydrolysates for fermentation. The processes used to produce these hydrolysates often result in the generation of chemical byproducts that inhibit cell growth and fermentation. Such inhibitors include salts, furfural, hydroxymethyl furfural (HMF), acetic, ferulic, glucuronic, and r-coumaric acids, and phenolic compounds. (Qureshi et al. Economics of butanol fermentation using hyper-butanol producing *Clostridium beijerinckii* BA101. Food and bioproducts processing, Vol. 78(3), 2000: 139-144; Tao et al. Comparative techno-economic analysis and reviews of n-butanol production from corn grain and corn stover. Biofuels, Bioproducts and Biorefining, Vol. 8(3), 2014: 342-361). Thus, the conversion of renewable lignocellulosic waste biomass and their by-products (e.g. low value agro-industrial wastes, municipal organic etc.) to bio-butanol is the key step to provide an affordable and sustainable solution to the oil crisis and energy sector (Maiti et al. Agro-industrial wastes as feedstock for sustainable bio-production of butanol by *Clostridium beijerinckii*. Food and Bioproducts Processing, Vol. 98, 11 Jan. 2016: 217-226).

Food waste includes unconsumed food that is discarded by food processing industries, retailers, restaurants, and consumers. Most of the food industry wastes find no current uses different from landfilling or first-generation recycling practices, such as animal feed, composting and incineration (Lin et al. Food waste as a valuable resource for the production of chemicals, materials and fuels. Current situation and global perspective. Energy Environmental Sci., Vol. 6(2), 2013: 426-464). Dhillon, G. S., Brar, S. K., Verma, M., Tyagi, R. D., 2011. Utilization of different agro-industrial wastes for sustainable bioproduction of citric acid by *Aspergillus niger*. Biochemical Engineering Journal 54, 83-92. Dhillon, G. S., Kaur, S., Brar, S. K., 2013. Perspective of apple processing wastes as low-cost substrates for bioproduction of high value products: A review. Renewable and Sustainable Energy Reviews 27, 789-805. (Dhillon et al. Enhanced solid-state citric acid bio-production using appled pomace waste through surface response methodology. Journal of Applied Microbiology, Vol. 110, 2011: 1045-1055). Disposal of food waste in landfill or incineration can cause severe amount of greenhouse gases ($CH_4$ and $CO_2$) Composting is getting popular, as it diverts food waste from landfill and improves soil structure. However, this type of practice is still carried out at a relatively elevated cost, and has a potential problem of pollution to surface and underground water. In light of the above comments, effective utilization of food waste for fuels and chemicals will positively influence the energy and environmental sustainability, and the economic competitiveness. Beer is the most appreciated and consumed beverage. Worldwide beer production process generated in thousands of tons of carbon rich organic wastes such as brewery spent grain (BSG) and brewery liquid wastes (BLW) in every year. (Maiti et al.

Agro-industrial wastes as feedstock for sustainable bio-production of butanol by Clostridium beijerinckii. Food and Bioproducts Processing, Vol. 98, 11 Jan. 2016: 217-226).

The brewing sector holds a strategic economic position in the food industry. The annual world beer production exceeding 1.34 billion hectolitres was reported in 2002 (Fillaudeau et al. Water, wastewater and waste management in brewing industries. Journal of Cleaner Production, Vol. 14(5), 2006). Canada produces a large amount of beer (with an estimated 21.9 million hectoliters per year) that leads to an abundance of brewery wastes (Maiti et al., January 2016; Olajire. The brewing industry and environmental challenges. Journal of cleaner production, Vol. 30, 2012). During beer production, three (bio) chemical reactions (mashing, boiling, fermentation-maturation) and three other solid-liquid separations (wort separation, wort clarification and rough beer clarification) are required, generating a large amount of solid residues (brewery spent grain—BSG) and wastewater (brewery liquid waste—BLW) (Fillaudeau et al., 2006). About 3.5-4.4 L of water is required as brewing water for each litre of beer produced, while contaminated wastewater volume constitutes approximately 25% of the total volume of water consumed (Mielcarek et al. Biodegradability evaluation of wastewaters from malt and beer production. Journal of the Institute of Brewing, Vol. 119(4), 2013: 242-250). Besides, brewer's spent grain from the fermentation process is the most abundant brewing by-product, corresponding to around 85% of the total residues generated. Normally during beer production around 14 kg of spent grain was generated per hectolitres of beer (Olajire, 2012). Currently, it is only sold or given free as an animal feedstock (low value product) to reduce costs and provide added revenue (Mussatto et al. Techno-economic analysis for brewer's spent grains use on a biorefinery concept: The Brazilian case. Bioresource technology, Vol. 148, 2013: 302-310). Taking into account that Québec holds 21.2% of the Canadian industry breweries (constitutes the 1.5% of gross domestic product (GDP) (IBIS World Industry Report, 2015), the sanitation of wastewater effluent and efficient management of spent grain or trub (protein and hops left in kettle) accumulated during beer production is a real challenge of great social, environmental and economic value in this region.

Solid waste as well as effluents from brewery industries also threaten environment as these are usually used in land filling. During brewery fermentation cellulose, hemicellulose, and protein components of biomass remain unutilized. These residual organic matters on microbial degradation cause foul smell, evolve greenhouse gases and increase acidity of soil. Thus loss of potential biomasses occurs with adverse impact on environment.

Agro-based industries are experiencing a surge in their growth around the globe (Dhillon et al., 2013). Worldwide statistical data on these highly abundant agro-industrial waste production have been reported previously (Maiti et al., January 2016). Federation of Indian Chambers of Commerce and Industry report (2011) has showed that about 60-70% was discharged in the environment without any treatment and the rest was utilised for anaerobic digestion in Latin America, Eastern Europe, Africa, and Asia (except Japan) (Global Methane Initiative. (2011). Resource assessment for livestock and agro-industrial wastes—India.).

Previously, (Gassara et al. Pomace waste management scenarios in Québec—impact on greenhouse gas emissions. Journal of hazardous materials, Vol. 192(3), 2011: 1178-1185) it was reported that in Canada the utilization of agro-industrial wastes, such as fruit wastes, to obtain high added value bio-products was the least polluting option in terms of GHG emissions in comparison with landfill disposal, incineration and composting. In this context, bio-butanol production based on inexpensive agro-industrial waste is a promising renewable energy source for a country with abundant biomass resources, such as Canada in-order to reduce their noxious effect in the environment (Maiti et al., January 2016).

Nevertheless, even though research on bio-butanol upstream and downstream processing has significantly progressed, the naturally abundant Clostridia are still not able to efficiently hydrolyse lignocellulosic based agro-industrial waste (Ezeji et al. Bioproduction of butanol from biomass: from genes to bioreactors. Current opinion in biotechnology, Vol. 18(3), 2007: 220-227). The conversion of complex biomass into energy and biofuels requires effective utilization of $C_5$ and $C_6$ sugars present in hemicellulose, cellulose and starch by either processing these fractions together or separating and processing them separately (Gürbüz et al. Conversion of hemicellulose to furfural and levulinic acid using biphasic reactors with alkylphenol solvents. ChemSusChem, Vol. 5(2), 2012: 383-387). Unfortunately, the common industrial pretreatment method, i.e. diluted Brønsted acid thermo-hydrolysis, generates a complex combination of microbial inhibitors, such as weak acids (acetic acid and levulinic acid), furan derivatives (e.g., furfural, hydroxymethyl furfural (HMF)) and a mixture of phenolic compounds (e.g., vanillin, vanillic acid, syringaldehyde, ferulic acid) which inhibit and thus diminish the bio-butanol production. Significant detrimental effects of reported microbial inhibitors and their modes of action are shown in Table 1.

Individual inhibitory actions of these compounds and their potential synergistic effects hinder bacterial growth and sugar conversion, as energy is diverted to maintenance and cell-repair by four main coping mechanisms (detoxification, efflux, repair and tolerance), making detoxification a compulsory step to enhance bio-butanol production (Jonsson et al. Bioconversion of lignocellulose: inhibitors and detoxification. Biotechnology for biofuels, Vol. 6, Issue 1, 2013: 1; Piotrowski et al. Death by a thousand cuts: the challenges and diverse landscape of lignocellulosic hydrolysate inhibitors. Frontiers in Microbiology, Vol 5, 2014: 90). Different detoxification techniques previously tested and enlisted in Table 2 could be expensive and laborious processes and may reduce titre of total fermentable sugars. In this context, development of a simple, rapid and highly selective detoxification method would be highly desirable.

TABLE 1

Inhibitory concentration of different hydrolysis process by-products and their effect in ABE fermentation.

| Inhibitor | Concentration (g/L) | Effect of inhibitor in ABE production | Effect in microbial cell | References |
|---|---|---|---|---|
| HMF Furfural | >2-3 | 1. (<0.5 g/L) enhanced production and productivity<br>2. (≈2-3 g/L) converted to other less toxic acids by specific microorganism | 1. Adverse effect on enzymes required for metabolism and long lag phase during cell growth<br>2. Strong inhibition on ADH (anti-diuretic | (Zhang et al. New Biotechnology, 1(3), 2012) |

TABLE 1-continued

Inhibitory concentration of different hydrolysis process by-products and their effect in ABE fermentation.

| Inhibitor | Concentration (g/L) | Effect of inhibitor in ABE production | Effect in microbial cell | References |
|---|---|---|---|---|
| | | 3. (>3 g/L) was deleterious for ABE fermentation | hormone) led to accumulation of acetaldehyde (>0.5 mM), which inhibited DNA and protein synthesis<br>3. Membrane permeability decreased and deactivated cell replication | |
| Syringaldehyde | >0.05 | 1. (0.05 g/L) showed strong inhibition on cellulase enzyme activity<br>2. (0.3-1.0 g/L) stopped ABE production | 1. Disrupted electrochemical gradient by transporting protons back across the mitochondrial membranes | (Cho et al. Applied microbiology and biotechnology, 83(6), 2009) |
| Ferulic acid | >0.3 | 1. (>0.3 g/L) inhibited butanol production | 2. Deteriorated cell membranes' ability to serve as selective barriers and enzyme matrices, causing adverse effect in cell growth and sugar assimilation | |
| Vanillic acid | >1 | 1. (>1 g/L) stopped bio-butanol production<br>2. (>2.1 g/L) of total soluble phenolic compounds had strong negative effect in bio-butanol production | | |
| Vanillic | >1 | 1. (≈1 g/L) inhibited completely bio-butanol production | | |
| Soluble lignin | >0.7-0.8 | 1. (>0.74 g/L) Incomplete sugars utilization<br>2. (>0.92 g/L) Poor bio-butanol production (0.4 g/L); Accumulation of acetic and butyric acid (~3-4 fold) in comparison with control samples<br>3. (>1.77 g/L) stopped fermentation process | 1. Increased cell membrane fluidity, causing leakage of cellular contents, disrupting the cell redox balance and causing acid crash | (Liu et al. Bioresource technology, 189, 2015; Wang et al. Process Biochemistry, 46, 2011; Zhang et al. *Bioprocess and biosystems engineering*, 37(5), 2014) |

TABLE 2

Detoxification methods reported in the literature

| Technique | Reagent | Temperature (° C.) | Time (min) | Inhibitor reduction (%; [g/L]) | FSC*** reduction (%) | Substrate | Bacteria | Ref. |
|---|---|---|---|---|---|---|---|---|
| Electro-dialysis | — | N.M.* | N.M. | Furfural (7; 0.03)<br>5-HMF (7; ≈0.15)<br>Acetic acid (100; 1.84)<br>TPC** (70; ≈2) | 0 | Mixed softwood | N.M. | (Lee et al. Journal of Industrial and Engineering Chemistry, 19(6), 2013) |
| Electro-dialysis | — | N.M. | N.M. | Formic acid (100; 6.9)<br>Levulinic acid (100; 6.1) | 17 | Red algae | K. marxianus | (Wu et al. Journal of microbiology and biotechnology, 24(9); 2014) |
| Neutralization | CaO | 60 | 30 | Furfural + 5-HMF (42; 0.33) | 9 | Sunflower seed hull | Pichia stipites | (Telli-Okur et al. Bioresource technology, 99(7), 2008) |
| Neutralization | N.M. | N.M. | N.M. | Levulinic acid (12; 0.73) | 25 | Red algae | K. marxianus | (Wu et al., 2014) |
| Overliming | CaO | 60 | 30 | Furfural + 5-HMF (41; 0.32) | 12 | Sunflower seed hull | Pichia stipites | (Telli-Okur et al., 2008) |
| Overliming | Ca(OH)$_2$ | N.M. | 60 | Furfural (20; 0.20)<br>5-HNF (22; 1.30) | 0 | Spruce | Saccharomyces cerevisiae | (Larsson et al. Applied biochemistry and biotechnology 77(1-3), 1999) |
| Overliming | Ca(OH)$_2$ | 60 | 30 | Formic acid (52; 3.59)<br>Levulinic acid (48; 2.93) | 42 | Red algae | K. marxianus | (Wu et al., 2014) |
| Overliming | Ca(OH)$_2$ | 60 | 60 | p-Coumeric acid (34; 0.35) | N.M. | Olives stone | N.M. | (Andary et al., 2013) |
| Overliming | Na$_4$OH | 80 | 180 | Furfural (93; 0.75)<br>5-HMF (89; 2.76) | Glucose 25<br>Mannose 16 | Spruce | Saccharomyces cerevisiae | (Larsson et al., 1999) |
| Overliming | Na$_2$SO$_3$ in helium atmosphere | N.M. | 60 | Furfural (53; 0.53)<br>5-HMF (52; 3.07) | 0 | Spruce | Saccharomyces cerevisiae | |
| Absorption | Treated charcoal (prepared at | Room | >300 | Furfural (100; 0.26)<br>5-HMF (100; 0.490)<br>Vanillic acid (100; 0.33) | 0 | Spruce chips | Saccharomyces cerevisiae | (Miyafuji et al. Enzyme and Microbial |

TABLE 2-continued

Detoxification methods reported in the literature

| Technique | Reagent | Temperature (° C.) | Time (min) | Inhibitor reduction (%; [g/L]) | FSC*** reduction (%) | Substrate | Bacteria | Ref. |
|---|---|---|---|---|---|---|---|---|
| | | 600° C.) | | Vanillin (100; 0.36) | | | | Technology, 32(3), 2003) |
| Overliming + Absorption | CaO + charcoal | 30 | 24 | Furfural + 5-HMF (68; 0.53) | 11 | Sunflower seed hull | Pichia stipites | (Telli-Okur et al., 2008) |
| Overliming + Filtration + Absorption | CaO + Activated charcoal | Overliming (100) + absorption (40) | Overliming (15) + absorption (60) | Acetic acid (28; 3.0) TPC (97; 0.95) | Glucose 18 Xylose 28 Arabinose 9 | Corn cob hemicellulose | C. shehatae ACCC 20335 | (Ge et al. African Journal of Microbiology Research, 5(10), 2011) |
| Evaporation | — | N.M. | Until 90% of evaporation | Furfural (100; 1.0) 5-HMF (4; 0.24) Acetic acid (65; 1.56) Formic acid (74; 1.18) | 0 | Spruce | Saccharomyces cerevisiae | (Larsson et al., 1999) |
| Surfactant-based cloud point extraction (CPE) | Non-toxic thermoseperating copolymer (L62D 5%) | N.M. | N.M. | Furfural (30; ≈0.15) 5-HMF (≈10%; ≈0.1) p-Coumeric acid (90; 0.45) Vanillin (100; ≈0.5) Ferulic acid (100; ≈0.5) Syringaldehyde (100; ≈0.5) | 0 | Corn stover | — | (Dhamole et al. Journal of Chemical Technology and Biotechnology, 88(9), 2013) |
| Extraction + roto-evaporation | Ethyl acetate (1:1)-4 times | N.M. | N.M. | Furfural (100; 0.28) HBA (100; 1.07) Vanillin (100; 0.21) | Glucose 6 Xylose 19 | Aspenwood chips | Pichiastipitis CBS 5776 | (Wilson et al. Applied microbiology and biotechnology, 31(5-6), 1989) |

*N.M.: Not mentioned;
**TPC: Total phenolic compounds;
**FSC: Fermen Table sugar concentration

SUMMARY

According to an embodiment, there is provided a process for extracting a microbial inhibitor from a hydrolysate of glycosidic waste matter containing free reducing sugars prior to a fermentation reaction, the process comprising the step of:
solvent extraction of the hydrolysate with a solvent selected from the group consisting of bis-(2-ethylhexyl) sebacate, 2-undecanone, and a combination thereof, over a period of sufficient length to extract the microbial inhibitor therefrom, thereby obtaining an extract containing the microbial inhibitor and reducing the level of the microbial inhibitor in the hydrolysate.

According to another embodiment, there is provided a process for the production of bio-butanol by fermentation of a detoxified hydrolysate of glycosidic waste matter containing free reducing sugars, the process comprising the step of:
fermentation of the detoxified hydrolysate with a solventogenic microorganism over a period of sufficient length and at a temperature sufficient to produce the bio-butanol, wherein the detoxified hydrolysate is obtained from a solvent extraction of a hydrolysate of glycosidic waste matter containing free reducing sugars with a solvent selected from the group consisting of bis-(2-ethylhexyl) sebacate, 2-undecanone, and a combination thereof, over a period of sufficient length to extract a microbial inhibitor therefrom, thereby obtaining an extract containing the microbial inhibitor and the detoxified hydrolysate.

The process may further comprise the step of:
solvent extraction of a hydrolysate of glycosidic waste matter containing free reducing sugars with a solvent selected from the group consisting of bis-(2-ethylhexyl) sebacate, 2-undecanone, and a combination thereof, over a period of sufficient length to extract a microbial inhibitor therefrom, thereby obtaining an extract containing the microbial inhibitor and the detoxified hydrolysate.

The hydrolysate of glycosidic waste matter containing free reducing sugars may be a hydrolysate of cellulosic waste matter containing free reducing sugars, a hydrolysate of amylosic waste matter containing free reducing sugars, or a combination thereof.

The hydrolysate of glycosidic waste matter containing free reducing sugars may be obtained from cellulosic waste matter, amylosic waste matter, or a combination thereof.

The cellulosic waste matter may be obtained from brewery liquid waste, brewery spent grain, apple pomace ultrafiltration sludge, apple pomace solid waste, or combinations thereof.

The amylosic waste matter may be from starch industry wastewater.

The solvent may be bis-(2-ethylhexyl) sebacate.

The solvent may be 2-undecanone.

The ratio of hydrolysate of glycosidic waste matter containing free reducing sugars to solvent ($v_{aqueous}:v_{organic}$) may be from 5:1 to 1:2.

The ratio may be 2:1.

The ratio may be 5:1.

The ratio may be 3:1.

The ratio may be 1:1.

The ratio may be 1:2.

The process may comprise mixing of the hydrolysate and the solvent during solvent extraction.

The mixing may be performed using a propeller impeller.

The mixing may be performed by providing an input of energy from 0.02 to 0.12 W·h/L.

The period of sufficient length to extract the microbial inhibitor may be from 15 to 60 minutes.

The time sufficient to extract the microbial inhibitor may be 30 minutes.

The solvent extraction may be performed at a temperature from 15° C. to 30° C.

The temperature sufficient for the solvent extraction may be room temperature (25° C.).

The solvent extraction may comprise separating the obtained hydrolysate from the solvent using at least one of a funnel separation, a centrifugal force-assisted separation, and a combination thereof.

The obtained hydrolysate may be produced by hydrolysis of glyosidic waste matter, the hydrolysis comprising at least one of a chemical hydrolysis, a thermal hydrolysis, an enzymatic hydrolysis, a mechanical hydrolysis, and combinations thereof.

The obtained hydrolysate may be produced by the thermal hydrolysis of the glycosidic waste matter, the thermal hydrolysis comprising at least one of a microwave-assisted hydrolysis and an autoclave-assisted hydrolysis.

The hydrolysis may be performed under a pressure of 89 kPa to 110 kPa.

The hydrolysis may be performed at a pH of about 0.32 to about 10.

The hydrolysis may be performed at a temperature greater than 100° C.

The hydrolysis may be performed at pH 0.76 in $H_2SO_4$, at 121° C., 16 psi (110.3 kPa), for 40 mins.

The thermal hydrolysis may be a Brønsted acid catalyzed pressurized thermal hydrolysis.

The Brønsted acid catalyzed pressurized thermal hydrolysis may be performed using $H_2SO_4$, HCl, betaine hydrochloride, $H_2O_2$, or combinations thereof.

The acid concentration may be from about 2 N to about 8.7 N.

The thermal hydrolysis may be an alkali catalyzed hydrolysis.

The alkali may be NaOH.

The alkali concentration may be from about 1 N to about 2 N.

The mechanical hydrolysis may be an ultra-sonication.

The fermentation may be performed at a temperature from 30° C. to 40° C.

The fermentation may be performed at a temperature of 37° C.

The fermentation may be performed in batch mode for at least 48 hours.

The fermentation may be performed in batch mode for 72 hours.

The fermentation may be performed under agitation.

The solventogenic microorganism may comprise a clostridia bacteria.

The clostridia bacteria may comprise at least one of *Clostridium acetobutylicum* NRRL B-582, *Clostridium beijerinckii* NRRL B-466 and a combination thereof.

The following defines some of the terms used throughout the specification. Where the provided definition of a term departs from the commonly used meaning of the term, applicant intends to use the provided definition in the absence of an explicit indication to the contrary.

The term "bio-butanol" is intended to mean butanol that has been produced from biomass. Bio-butanol is produced by a microbial fermentation, similar to ethanol and can be made from the same range of sugar, starch or cellulosic feedstocks. According to the present invention it is generated from hydrolyzed glycosidic (e.g. cellulosic or amylosic) waste matter.

The term "glycosidic waste matter" or "glycosidic matter" is intended to mean matter that comprises carbohydrate molecules that contain glycosidic bonds of natural origins, such as for example cellulosic and/or amylosic material from plants. Preferably, the matter is chosen from brewery liquid waste (BLW), brewery spent grain (BSG), apple pomace ultrafiltration sludge (APUS), apple pomace solid waste (APS), starch industry wastewater (SIW) or combinations thereof.

The term "bioreactor" is intended to mean an apparatus in which a biological reaction or process is carried out. This includes small, medium and large (industrial) scale apparatuses.

The term "fermentation medium" is intended to mean a growth medium in which fermentation by suitable microorganism such as bacteria, yeast and fungi to make useful products can take place. In some embodiments, the fermentation medium may be supplemented with several different kinds of additives (see below).

The term "fermentation mixture" is intended to mean a combination of the fermentation medium and the microorganisms.

The term "solventogenic microorganism" is intended to mean a microorganism that is capable of producing a solvent, such as ethanol, butanol, or other, and include for example Clostridia bacteria such as *Clostridium acetobutylicum* NRRL B-582, *Clostridium beijerinckii* NRRL B-466, *Clostridium acetobutylicum*, *Clostridium beijerinckii*, *Clostridium saccharobutylicum*, and *Clostridium saccharoperbutylacetonicum*, *Clostridium Bezrinckii* BA101, Clostridia strain TU-103, yeasts, genetically engineered *Pseudomonas putida* DOT-T1E, genetically engineered *Bacillus subtilis* GRSW2-B1, genetically engineered *B. subtilis* 168 and *B. subtilis* KS438, as well as other solventogenic recombinant bacteria and microorganisms, or combinations thereof.

The term "solventogenic production conditions" is intended to mean fermentation conditions that are suitable for the production of solvents (e.g. bio-butanol) by the selected solventogenic microorganism. Such conditions include for example the appropriate temperature, pH, nutrient and salt condition, agitation, pressure as well as any other suitable and/or necessary condition required to achieve hydrogen production under fermentative conditions.

The terms "detoxification", or "detoxified" is intended to mean the removal or the decrease of their levels in a hydrolysate of glycosidic waste matter so as to lift their inhibitory effect on the fermentation of the matter.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

BRIEF DESCRIPTION OF THE DRAWINGS

Further features and advantages of the present disclosure will become apparent from the following detailed description, taken in combination with the appended drawings, in which.

DETAILED DESCRIPTION

Figure 1:
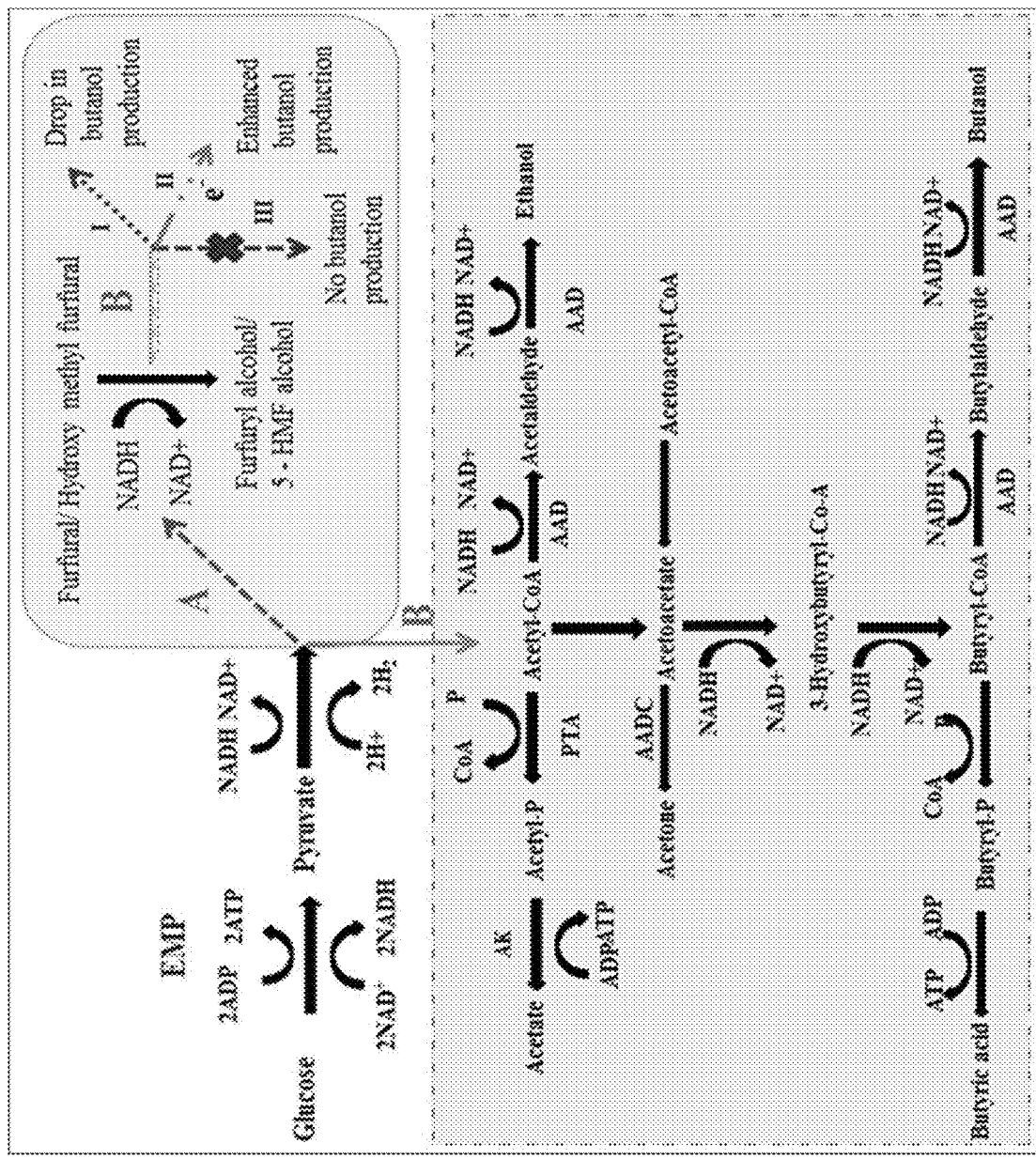
FIG. 1 illustrates biochemical pathways for fermentation and inhibition thereof according to an embodiment of the present invention. A: Effects of furan derivatives inhibitors during ABE fermentation. B: Pathway for anaerobic (acetone-ethanol-butanol) ABE fermentation. I: Furfural/5-HMF (<0.5 g/L) enhanced production and productivity. II: Furfural/5-HMF (≤2-3 g/L) dropped in production and productivity. III: Furfural/5-HMF (>3 g/L) was deleterious for ABE fermentation.

In one embodiment there is disclosed a process for extracting a microbial inhibitor from a hydrolysate of glycosidic waste matter containing free reducing sugars prior to a fermentation reaction, the process comprising the step of: solvent extraction of the hydrolysate with a solvent selected from the group consisting of bis-(2-ethylhexyl) sebacate, 2-undecanone, and a combination thereof, over a period of sufficient length to extract the microbial inhibitor therefrom, thereby obtaining an extract containing the microbial inhibitor and reducing the level of the microbial inhibitor in the hydrolysate.

In another embodiment, there is disclosed a process for the production of bio-butanol by fermentation of a detoxified hydrolysate of glycosidic waste matter containing free reducing sugars, the process comprising the step of: fermentation of the detoxified hydrolysate with a solventogenic microorganism over a period of sufficient length and at a temperature sufficient to produce the bio-butanol, wherein the detoxified hydrolysate is obtained from a solvent extraction of a hydrolysate of glycosidic waste matter containing free reducing sugars with a solvent selected from the group consisting of bis-(2-ethylhexyl) sebacate, 2-undecanone, and a combination thereof, over a period of sufficient length to extract a microbial inhibitor therefrom, thereby obtaining an extract containing the microbial inhibitor and the detoxified hydrolysate.

The process may further comprise the step of: solvent extraction of a hydrolysate of glycosidic waste matter containing free reducing sugars with a solvent selected from the group consisting of bis-(2-ethylhexyl) sebacate, 2-undecanone, and a combination thereof, over a period of sufficient length to extract a microbial inhibitor therefrom, thereby obtaining an extract containing the microbial inhibitor and the detoxified hydrolysate In another embodiment, there is disclosed a process for the production of bio-butanol from fermentation of a hydrolyzed glycosidic waste matter containing free reducing sugars, the process comprising the step of: solvent extraction of a hydrolysate of a glycosidic waste matter containing free reducing sugars with a solvent selected from the group consisting of bis-(2-ethylhexyl) sebacate, 2-undecanone, and a combination thereof, over a period of sufficient length to extract a microbial inhibitor therefrom, thereby obtaining an extract containing the microbial inhibitor and a hydrolyzed glycosidic waste matter containing free reducing sugars; and
fermentation of the hydrolyzed glycosidic waste matter containing free reducing sugars with a solventogenic microorganism for over a period of sufficient length and at a temperature sufficient to produce the bio-butanol.

Waste Matter

In embodiments of the process of the present invention, the hydrolyzed glycosidic waste matter containing free reducing sugars may be a hydrolyzed cellulosic waste matter containing free reducing sugars, a hydrolyzed amylosic waste matter containing free reducing sugars, or a combination thereof. In embodiments, the hydrolyzed glycosidic waste matter containing free reducing sugars may be obtained from a cellulosic waste matter, an amylosic waste matter, or a combination thereof. The cellulosic waste matter may be from, for example, brewery liquid waste, brewery spent grain, apple pomace ultrafiltration sludge, apple pomace solid waste, or combinations thereof. The amylosic waste matter may be from, for example, starch industry wastewater.

Extraction Solvents and Conditions

According to these embodiments, the solvent may be selected from the group consisting of bis-(2-ethylhexyl) sebacate, 2-undecanone, and a combination thereof. In the process, the ratio of hydrolyzed glycosidic waste matter containing free reducing sugars (the aqueous phase) to solvent (the organic phase) ($V_{aqueous}:V_{organic}$) is from 5:1 to 1:2, or from 5:1 to 1:1, or from 5:1 to 2:1, or from 5:1 to 3:1, or 3:1 to 1:2, or from 3:1 to 1:1, or from 3:1 to 2:1, or 2:1 to 1:2, or from 2:1 to 1:1, or from 5:1, or from 3:1, or from 2:1, or from 1:1, or from 2:1, and preferably 2:1.

According to an embodiment, the processes of the present invention comprise mixing of the hydrolyzed glycosidic waste matter containing free reducing sugars and the solvent during solvent extraction, in order to increase extraction of the inhibitor found in the hydrolyzed glycosidic waste matter. In embodiments, the mixing may be effected with a propeller impeller, although any suitable device to mix the components will be adequate. The input of energy for mixing may be from 0.02 W·h/L to 0.12 W·h/L, or from 0.04 W·h/L to 0.12 W·h/L, or from 0.06 W·h/L to 0.12 W·h/L, or from 0.08 W·h/L to 0.12 W·h/L, or from 0.1 W·h/L to 0.12 W·h/L, or from 0.02 W·h/L to 0.10 W·h/L, or from 0.04 W·h/L to 0.10 W·h/L, or from 0.06 W·h/L to 0.10 W·h/L, or from 0.08 W·h/L to 0.10 W·h/L, or from 0.02 W·h/L to 0.08 W·h/L, or from 0.04 W·h/L to 0.08 W·h/L, or from 0.06 W·h/L to 0.08 W·h/L, or from 0.02 W·h/L to 0.06 W·h/L, or from 0.04 W·h/L to 0.06 W·h/L, from 0.02 W·h/L to 0.04 W·h/L. The time sufficient to extract the microbial inhibitor is from 15 to 90 minutes, or from 30 to 90 minutes, or from 45 to 90 minutes, or from 60 to 90 minutes, or from 15 to 60 minutes, or from 30 to 60 minutes, or from 45 to 60 minutes, or from 15 to 45 minutes, or from 30 to 45 minutes, or from 15 to 30 minutes, or 15, 30, 45, 60, or 90 minutes.

In embodiments, the process of the present invention may be performed at a temperature sufficient for the solvent extraction. Suitable temperatures may include temperatures from 15° C. to 30° C. In a preferred embodiment, the temperature sufficient for the solvent extraction is room temperature (25° C.).

According to embodiments, the extraction is completed by the separation of the aqueous and organic phases from one another. Separation may be a funnel separation, a centrifugal force assisted separation, or a combination thereof, such that the hydrolyzed glycosidic waste matter containing free reducing sugars and the solvent are separated.

Hydrolysis Conditions

According to an embodiment, in the process of the present invention, the hydrolyzed glycosidic waste matter containing free reducing sugars may be produced by a chemical hydrolysis, a thermal hydrolysis, an enzymatic hydrolysis, a mechanical hydrolysis, or a combination thereof, of the glycosidic waste matter. According to an embodiment, the thermal hydrolysis may be a microwave hydrolysis.

In embodiments, the hydrolysis may be performed under a pressure of 89 kPa to 110 kPa.

In embodiments, the hydrolysis is performed at a pH of about 0.32 to about 10

In embodiments, the hydrolysis is performed at a temperature of greater than 100° C.

In embodiments, the hydrolysis is performed at pH 0.76 in $H_2SO_4$, at 121° C., 16 psi (110.3 kPa), for 40 mins.

The thermal hydrolysis may also be a Brønsted acid catalyzed pressurized thermal hydrolysis. The Brønsted acid catalyzed pressurized thermal hydrolysis may be performed with $H_2SO_4$, HCl, betaine hydrochloride, $H_2O_2$, or combinations thereof. The acid concentration may be from about 2 N to about 8.7 N.

In embodiments, the thermal hydrolysis may be an alkali catalyzed hydrolysis. The alkali may be NaOH. The alkali concentration may be from about 1 N to about 2 N.

In embodiments, the mechanical hydrolysis may be an ultra-sonication.

In embodiments, the fermentation is performed at a temperature from 30° C. to 40° C.

In embodiments, the fermentation is performed at a temperature of 37° C.

In embodiments, the fermentation is performed for in batch mode for at least 48 hours.

In embodiments, the fermentation is performed in batch mode for 72 hours.

In embodiments, the fermentation is performed under agitation.

Solventogenic Microorganisms

In embodiments, the solventogenic microorganism is a clostridia bacteria. According to preferred embodiments, the clostridia bacteria is *Clostridium acetobutylicum* NRRL B-582, *Clostridium beijerinckii* NRRL B-466 *Clostridium acetobutylicum*, *Clostridium beijerinckii*, *Clostridium saccharobutylicum*, and *Clostridium saccharoperbutylacetonicum*, *Clostridium Bezrinckii* BA101, Clostridia strain TU-103, yeasts, genetically engineered *Pseudomonas putida* DOT-T1E, genetically engineered *Bacillus subtilis* GRSW2-B1, genetically engineered *B. subtilis* 168 and *B. subtilis* KS438, as well as other solventogenic recombinant bacteria and microorganisms, or a combination thereof.

In these examples, a two-phase partitioning extraction was considered as an efficient alternative to reduce microbial inhibitors harmful effects. Two-phase partitioning bioreactor systems (TPPBs) were devised in the early 1990s for off-gas biological-treatment in order to increase the mass transfer of low hydrophobic volatile organic compounds (VOC) from the gas phase to the microorganisms and to reduce the microbial inhibition due to the presence of high VOC or toxic metabolite concentrations (Muñoz et al. Recent advances in two-phase partitioning bioreactors for the treatment of volatile organic compounds. Biotechnology advances, Vol. 30(6), 2012: 1707-1720). Hence, the objectives of these examples were: (1) to investigate the capacity of organic solvents to remove typical lignocellulosic hydrolysate microbial inhibitors, (2) to identify the best solvent with higher removal efficiency with no toxic effect on solventogenic Clostridia bacteria, (3) to optimize different process parameters to enhance inhibitors removal efficiency from a real brewery industry hydrolysate as glycosidic material in order to improve bio-butanol production, (4) to estimate the power consumption for cost-effective production scale-up, (5) to investigate alternative glycosidic materials, and (6) to compare microwave and other alternative pretreatment techniques for hydrolysis.

The present invention will be more readily understood by referring to the following examples which are given to illustrate the invention rather than to limit its scope.

Example 1

Production of Bio-Butanol from Brewery Industrial Wastes 1.1 Microorganism and Inoculums Development

*Clostridium acetobutylicum* NRRL B-582 (ATCC-824) (CA) and *Clostridium beijerinckii* NRRL B-466(CB) were considered for current investigation to produce bio-butanol from different brewery industry wastes. They were kindly provided by Agricultural Research Station, USDA (USA). The microorganisms were grown and maintained in peptone-yeast extract-glucose (PYG) media under anaerobic condition (vegetative growth) at 37±1° C. and 150 rpm for 24 h and 17 h, respectively, before being transferred into the fermentation medium. The medium (g $L^{-1}$) comprised: glucose (10); yeast extract (10); peptone (5); tryptone (5); cysteine-HCl (0.5); $K_2HPO_4$ (2.04); $KH_2PO_4$ (0.04); $FeSO_4*7H_2O$ (1.1×10$^{-3}$); $CaCl_2$ (8×10$^{-3}$); $MgSO_4*7H_2O$ (0.0192); NaCl (0.08); and $NaHCO_3$ (0.4). 125 mL serum bottles (working volume 50 mL) were used for both butanol production and inoculum development (Maiti et al., January 2016, Maiti et al., August 2015). Anaerobic conditions were maintained within the bottle by sparging $N_2$ for 10 minutes and immediately sealed by an aluminum crimp seal containing silicone septum (Fisher scientific, Canada) by means of a hand operated crimper (E-Z Crimper™, VWR, Ontario, Canada). Prior to culture development, the medium was sterilized for 20 min at 121±1° C. About 10% (v/v) (dry cell weight 35-50 mg/mL) of microbial culture in its exponential phase of growth ($OD_{600nm}$=1.3-1.5) was used as inoculum for all the experiments conducted in this investigation.

1.2 Chemicals and Other Materials

Chemicals, such as glucose, urea, $MgSO_4*7H_2O$, NaOH, $FeSO_4.7H_2O$, $CaCl_2$), cysteine, NaCl, $NaHCO_3$, $Ca(OH)_2$, $Na_2SO_3$, $H_2SO_4$, n-butanol, acetone, acetic acid, butyric acid, ethanol, 2-undecanone (98%) and bis-(2-ethylhexyl) sebacate(98%) were purchased from Fisher Scientific (Ontario, Canada and New Jersey, USA). Vanillin, vanillic acid, feluric acid, furfural, HMF, acetic acid, levulinic acid, syringaldehyde, glucose, xylose, galactose and fructose were purchased from Sigma Aldrich (USA). All standards were of analytical grade. Casein peptone, tryptone, $K_2HPO_4$ and $KH_2PO_4$ were purchased from VWR (Ontario, Canada) and the yeast extract was a kind gift from Lallemand Inc. (Montreal, Canada). The substrates used in this example (i.e. brewery liquid waste (BLW) and brewery industry spent grains (BSG)) were generously provided by La Barberie Microbrasserie Cooperative de Travail (Québec, Canada).

1.3 Organic-Solvents Tested for Efficient Extraction of Microbial Inhibitors from an Agro-Waste Hydrolysate Mimic 2-undecanone and bis-(2-ethylhexyl) sebacate were tested for efficient extraction of a mixture of relevant inhibitors (furfural, 5-HMF, vanillic acid, vanillin, syringaldehyde and ferulic acid) from a synthetic media simulating a real agro-waste hydrolysate composed of 50-52 g/L glucose; 3.0-3.2 g/L of both furfural and HMF; 0.5 g/L of the other compounds (vanillic acid, vanillin, syringaldehyde and feluric acid). Media composition was designed according to the inhibitory compound limit concentration reported in the literature for bio-butanol producing solventogenic Clostridia (Baral et al. Microbial inhibitors: formation and effects on acetone-butanol-ethanol fermentation of lignocellulosic biomass. Applied microbiology and biotechnology, Vol. 98(22), 2014: 9151-9172; Qureshi et al. Production of butanol (a biofuel) from agricultural residues: Part I—Use of barley straw hydrolysate. Biomass and bioenergy, Vol. 34(4), 2010: 559-565). Different volume ratio of the hydrolysate mimic and organic solvents, such as (5:1), (3:1), (2:1), (1:1) and (1:2) ($V_{aqueous}$:$V_{organic}$) were tried in order to minimize extractant expenditure. Organic and aqueous phase mixing was carried out by a propeller impeller. Rotation rate (100, 200, 250, 300 and 400 rpm) and operation-time (15, 30, 45, 60 and 90 min) were tested at room temperature (25° C.). A comparative study between settling through separating funnel vs. centrifugal force assisted separation was also made to guarantee an optimal recovery of the broth phase.

1.4 Bio-Compatibility Study of Selected Organic-Solvents for Efficient Extraction of Microbial Inhibitors and Improved Bio-Butanol Production The main constraint of the extracting phase is that it must perform the inhibitor removal with preservation of the cell viability. In solvent toxicity tests, various sets of experiments were developed for both microorganisms as follows: set-1: (control-1) 52 g/L of glucose; set-2: control-1+(5-15)% 2-undecanone; set-3: control-1+(5-15)% bis-(2-ethylhexyl) sebacate; set-4: (control-2): 52 g/L glucose+bacterial inhibitory solution (BIS) (3.0-3.2 g/L of both furfural and HMF; 0.5 g/L of the other compounds (vanillic acid, vanillin, syringaldehyde and ferulic acid)); set-5: (control-3): (5-15)% of each organic extractant without glucose and BIS; set-6: 52 g/L glucose+5 times diluted BIS*; set-7: 52 g/L glucose+10 times diluted BIS*; set-8: 52 g/L glucose+50 times diluted BIS*; set-9: control-2+extraction (2:1=agro-waste hydrolysate mimic: organic solvent); set-10: Set-7+extraction (2:1=agro-waste hydrolysate mimic: organic solvent); set-11: Set-8+extraction (2:1=agro-waste hydrolysate mimic: organic solvent). Set-1, set-4 and set-5 were included as control-1, control-2 and control-3 respectively. All the experiments were carried out in $P_2$ nutrient media as described later in batch fermentation section.

1.5 Pretreatment of Real Agro-Industrial Wastes: Brewery Industry Liquid Waste (BLW) and Brewery Spent Grain (BSG)

Brewery liquid waste (BLW) was received in a semi-solid heterogeneous sludge state; while brewery spent grain (BSG) was a solid residue. In order to compare their performance, all the biomass was dried at 65±1° C. for 72 h prior to hydrolysis. Additionally, dried BSG was grinded to obtain a particle size below 20 mm. The composition of the dry feedstock is reported in Table 3. Both dried residues were pre-treated by means of a Brønsted acid-catalysed thermal hydrolysis in an autoclave (sulfuric acid ($H_2SO_4$) at a temperature of 121±1° C. for 40 minutes, pressure of 16 psi (110.3 kPa) and pH of 0.76) in order to allow cellulolytic enzymes access to the polysaccharide matrices.

TABLE 3

Physicochemical characterization of brewery industry wastes (dry weight basis).

| Components | Brewery spent grain | Brewery Liquid Waste | |
| --- | --- | --- | --- |
| | | Surplus yeast | Spent hops |
| pH | 5.2 ± 0.1 | 5.4 ± 0.1 | 5.1 ± 0.1 |
| Total Solid (g/L) | — | 229.4 ± 1.5 | — |
| Ash content (%) | 7.8 ± 0.7 | 8.9 ± 1.4 | — |
| Extractive (%) | 3.5 ± 0.4 | 5.7 ± 0.6 | — |
| Carbohydrates (%) | — | 36.4 ± 1.5 | 40.0 ± 0.5 |
| Crude fiber (%) | — | 3.0 ± 1.5 | 26.5 ± 2.4 |
| Cellulose (%) | 17.1 ± 1.0 | — | — |
| Hemicellulose (%) | 32.5 ± 1.5 | — | — |
| Lignin (%) | 13.4 ± 1.9 | — | — |
| Free reducing sugar (g/kg) | 22.7 ± 5.3 | 102.8 ± 4.7 | — |
| Glucose (g/kg) | 1.6 ± 0.1 | 55.8 ± 1.3 | — |
| Fructose (g/kg) | — | — | — |
| Galactose (g/kg) | — | 5.9 ± 0.9 | — |
| Xylose (g/kg) | — | 5.7 ± 0.9 | — |
| Micronutrients (mg/kg) | | | |
| Cd | 7.3 ± 0.3 | 4.2 ± 0.7 | — |
| Al | 1099 ± 135 | 8677 ± 105 | — |
| Mn | 4464 ± 145 | 1551 ± 112 | — |
| Al | 1450 ± 186 | 8915 ± 256 | — |
| As | 13.9 ± 2.6 | 68.8 ± 5.0 | — |
| Ca | 243347 ± 124 | 310589 ± 156 | — |
| Co | 2.6 ± 0.0 | 25.2 ± 0.2 | — |
| Cr | 55.6 ± 1.6 | 49.8 ± 1.6 | — |
| Cu | 1120 ± 36 | 2126 ± 56 | — |
| Fe | 12069 ± 134 | 12077 ± 114 | — |
| K | 52330 ± 75 | 95476 ± 89 | — |
| Mg | 2096 ± 156 | 1878 ± 123 | — |
| Na | 11154 ± 107 | 23141 ± 92 | — |
| Ni | 87.5 ± 3.8 | 263.7 ± 23.6 | — |
| P | 69459 ± 145 | 10533 ± 178 | — |
| Pb | 3.9 ± 1.2 | 4.7 ± 0.5 | — |
| Se | 100.4 ± 32.1 | 123.3 ± 12.2 | — |
| Zn | 7312 ± 45 | 10527 ± 156 | — |

1.6 Detoxification of BLW and BSG Samples

Detoxification of BLW and BSG samples was carried out using two different already reported methods and the alternative method proposed herein. A modified version of the over liming method described by Martinez et al. (2001) was employed to detoxify both hydrolysates (Martinez et al. Detoxification of dilute acid hydrolysates of lignocellulose with lime. Biotechnology progress, Vol. 17(2), 2001: 287-293). The pH of the hydrolysate was adjusted to 10 with $Ca(OH)_2$ and later stored overnight at 30° C. The hydrolysate was mixed with 1 g/L $Na_2SO_3$ and the mixture was heated at 90±1° C. for 1 h. Subsequently, the precipitate of metal hydroxides was separated by centrifugation at 7650×g (30±1° C.) for 30 min. The precipitate so formed was discarded. The supernatant was neutralized to pH 6.7±0.1 with 1 M $H_2SO_4$ and centrifuged at 30±1° C. for 30 min at 7650×g to separate the precipitate.

In the detoxification method proposed by Ge et al. (2011), over liming with CaO (pH 7.0 and 100° C. for 15 min)+filtration+powdered activated charcoal (3% at 40° C. for 1 h and 200 rpm) was implemented (Ge et al. Comparison of different detoxification methods for corn cob hemicelluose hydrolysate to improve ethanol production by *Candida shehatae* ACCC 20335. African Journal of Microbiology Research, Vol. 5(10), 2011: 1163-1168). The precipitate form composed of metal hydroxides and charcoal was separated by centrifugation at 7650×g (30±1° C.) for 30 min. The supernatant was neutralized to pH 6.7±0.1 with 1 M $H_2SO_4$ and centrifuged at 30±1° C. for 30 min at 7650×g to separate the precipitate. In both already reported detoxification methods, the clear supernatant was used as the carbon source for the following fermentation studies. The alternative detoxification method proposed in this example consisted in an ex-situ organic extraction by means of bis-(2-ethylhexyl) sebacate ((2:1) $v_{hydrolysate}:v_{solvent}$) at 25° C. (room temperature), using a propeller impeller at 250 rpm as mixing mechanism followed by broth recovery through a separating funnel for 1 h. A propeller-type impeller was selected as it is used for low-viscosity liquid and it has been widely applied in vessels ranging from portable type to large tanks.

1.7 Batch Fermentation

Batch fermentation was performed in 125 mL serum vials (working volume of 50 mL) at pH 6.7±0.1. The $P_2$ medium was sterilized at 121±1° C. for 20 min. Prior to fermentation, anaerobic conditions for each bottle were maintained by sparging the medium with $N_2$ for 10 minutes and immediately closing with an aluminum crimp seal containing silicon septum (Fisher scientific, Canada) by means of a hand-operated crimper (E-Z Crimper™, VWR, Ontario, Canada). A modified $P_2$ medium, with the following composition, was used for fermentation experiments: Buffer→$KH_2PO_4$ 50 g/L, $K_2HPO_4$ 50 g/L, ammonium acetate 220 g/L; Minerals→$MgSO_4*7H_2O$ 20 g/L, $MnSO_4*H_2O$ 1 g/L, $FeSO_4*7H_2O$ 1 g/L, NaCl 1 g/L; Vitamins→thiamin 0.1 g/L, biotin 0.001 g/L). Since brewery industry wastes were already enriched with yeast protein, no additional yeast protein nor peptone were supplemented.

The fermentation was initiated by inoculating the $P_2$ medium with the seed cultures at a ratio of 10% (v:v). CA and CB bacterial strains were used for the experiments related to the bio-compatibility tests and CB was selected to carry out detoxification tests with real brewery industry hydrolysate wastes (BLW and BSG). Fermentation experiments were performed at 37±1° C. with shaking at 150 rpm for 72 h in duplicates. 1 mL of culture broth from each batch assay was used for metabolite analysis. Data described here present average values from duplicate runs for duplicate samples.

1.8 Total Reducing Sugars Determination

Total reducing sugars concentration (TRS) was determined by the di-nitro-salicylic acid method using glucose as the standard (Miller, Use of dinitrosalicylic acid reagent for determination of reducing sugar. Analytical chemistry, Vol. 31(3), 1959: 426-428). The amount of TRS extracted from hydrolyzed substrates was determined by UV-visible spectrophotometer (Cary-50, Varian) using 3,5-dinitrosalicylic acid as the reagent (DNS method) at 540 nm.

1.9 Microbial Inhibitors and Reduced Sugar Compounds Determination

A complex mixture of several reduced sugar compounds (e.g. as glucose, fructose, and xylose) and microbial inhibitors (furfural, HMF, acetic acid, levulinic acid, vanillin, vanillic acid, feluric acid and syringaldehyde) were produced during the pretreatment step (hydrolysis). In order to analyse these compounds, liquid samples were collected and analyzed using liquid chromatography-mass spectrometry (LC-MS) and liquid chromatography-tandem mass spectrometry (LC/MS-MS) equipped with a ZORBAX Carbohydrate column (5 µm, 150×4.6 mm ID column) (Agilent Technologies, USA) with $D_6$ glucose as the internal standard and a Biobasic-18 column (5 µm, 250×4.6 mm ID) (Agilent Technologies, USA) with phenylethanol-$D_5$ as the internal standard. Before injecting the sample, it was centrifuged for 5 minutes at 7650×g and the supernatant was filtered by 0.45 µm syringe filter. Methanol water (8:2) and acetonitrile water (8.5:1.5) were used to dilute the sample before inhibitor and carbohydrate analysis.

1.10 ABE (Acetone, Butanol, Ethanol) Fermentation Products Determination

To determine the different metabolites produced during ABE fermentation (i.e. butanol, ethanol, acetone, butyric acid, and acetic acid) liquid samples from each fermentation broth were collected and analyzed using gas chromatography (GC) (GC7890B, Agilent Technologies, USA) equipped with a FID detector and a HP-INNOWax™ column (30 m, 0.25 mm ID, 0.25 µm df). Isobutanol was used as the internal standard. Before injecting the sample (1 mL) in the GC for products analysis, the sample was centrifuged for 5 minutes at 7650×g and the supernatant was filtered by 0.45 µm syringe filter. The GC conditions comprised: helium carrier gas at a flow rate of 1 mL/min with a temperature ramp from the initial temperature of 50° C. to 150° C. (10° C./min) and from 150° C. to 250° C. (20° C./min) for a 16-min method run time at 11.421 psi (78.75 kPa). Removal of inhibitors from hydrolysate was calculated as (Eq. 1):

$$Removal\ (\%) = 100 \times \frac{Initial\ concentration\ of\ inhibitor\ (g/L) - final\ concentration\ of\ inhibitors\ after\ removal\ (g/L)}{Initial\ concentration\ of\ inhibitor\ (g/L)} \qquad (Eq.\ 1)$$

1.11 Results and Discussion 1.11.1 Organic-Solvent Used for Efficient Extraction of Microbial Inhibitors from an Agro-Waste Hydrolysate Mimic Presence of microbial inhibitors in agro-industrial waste hydrolysates favors lower production of bio-butanol (as shown in Table 1), even in presence of sufficient amount of reducing sugar compounds necessary to enable the exponential growth of cells (Maiti et al., January 2016, Ranjan et al. Biobutanol: science, engineering, and economics. International Journal of Energy Research, Vol. 36(3), 2012: 277-323). Conversion of inhibiting aromatic homo-cyclic phenolic compounds and heterocyclic furan derivatives to their corresponding less toxic substances leads to solventogenic (ABE) losses due to higher utilization of NADH in reduction of inhibitors instead of desired biosynthetic pathway of bio-butanol production (Ujor et al. Glycerol supplementation of the growth medium enhances in situ detoxification of furfural by Clostridium beijerinckii during butanol fermentation. Applied microbiology and biotechnology, Vol. 98(14), 2014: 6511-6521). To overcome the limitation encountered in biochemical production of bio-butanol due to the presence of microbial inhibitory compounds, a two-phase partitioning extraction was considered in the current example, a solution based on the addition of a non-aqueous phase, either a liquid solvent or a solid polymer, to a biological process. Thus, this detoxification method relies on the adequate selection of the extractant, which mainly depends on the characteristics of the microbial community present in the process and the characteristics of the inhibitors to be treated. Based on several requirements, such as higher affinity for the target pollutant, availability in bulk quantities (low cost), biocompatibility with Clostridia bacteria in order not to poison subsequent fermentation step, resistance to autoclaving and non-biodegradability, 2-undecanone and bis-(2-ethylhexyl) sebacate were selected for highly selective extraction of inhibitors from the aqueous phase.

The preliminary results about the optimum organic-aqueous phase volume ratio showed that increasing ratios implied higher extraction of inhibitory compounds for both organic solvents. In order to make the method more cost effective, the ratio (2:1) ($v_{aqueous}:v_{organic}$) was considered for further investigation since the results obtained were adequate enough for detoxification purpose (Table 4). In Table 4, the results for four consecutive extractions with each organic solvent are described. Inhibitor removal by bis-(2-ethylhexyl) sebacate was lower in comparison with 2-undecanone's capacity, whose extraction efficiency towards furan derivatives was about (87-90) % and higher than 95% for each phenolic compounds since the first stage. The selectivity of extraction with bis-(2-ethylhexyl) sebacate is slightly lower towards furan derivatives which was about 78-79% and phenolic compounds >93% Palmqvist et al., (2000), has previously reported that depending on the nature of lignocellulosic biomass, around about ~(4-5 g/L of furan derivative could be produced upon diluted acid hydrolysis (Palmqvist et al. Fermentation of lignocellulosic hydrolysates. II: inhibitors and mechanisms of inhibition. Bioresource technology, Vol. 74(1), 2000: 25-33). Thus the slightly incomplete extraction of furan derivatives recorded in the case of bis-(2-ethylhexyl) sebacate (78-79%) might even have a positive impact on anaerobic ABE fermentation, since the presence of furfural and HMF in the aqueous media in the range from ~(0.5 to 2.0) g/L has been proven to enhance bio-butanol production and productivity as they might act as fermentation precursors (Qureshi et al. Effect of cellulosic sugar degradation products (furfural and hydroxymethyl furfural) on acetone-butanol-ethanol (ABE) fermentation using *Clostridium beijerinckii* P260. Food and Bioproducts Processing, Vol. 90(3), 2012: 533-540; Zhang et al. Biotransformation of furfural and 5-hydroxymethyl furfural (HMF) by *Clostridium acetobutylicum* ATCC 824 during butanol fermentation. New Biotechnology, Vol. 1(3), 2012: 345-351).

While evaluating a detoxification treatment, the degradation of fermentable sugars is a major drawback that must be taken into account. Most of the methods reported so far in the literature involve a destruction of a certain percentage (up to 42%) of the total reducing sugar content (Table 2), which definitely has negative effect in ABE pathway as sugar is the main source of ATP to develop the ABE fermentation (Ranjan et al., 2012). No sugar degradation was observed for the current organic solvent extraction method (Table 4), which indicates the suitability of the detoxification treatment proposed.

TABLE 4

Organic-solvent screening for efficient extraction of microbial inhibitors from an agro-waste hydrolysate mimic.

| | HMF (g/L) | Furfural (g/L) | Vanillin (mg/L) | Vanillic acid (mg/L) | Syringaldehyde (mg/L) | Ferulic acid (mg/L) | |
|---|---|---|---|---|---|---|---|
| Extraction with 2-undecanone ($V_{aqueous}:V_{organic} = 2:1$) | | | | | | | |
| | | | | | | | TRS* (g/L) |
| Standard | 2.723 | 2.956 | 565.9 | 565.9 | 300.2 | 485.6 | 52.00 |
| Extraction 1 | 0.267 (90%) | 0.392 (87%) | 10.3 (98%) | 9.8 (95%) | 7.6 (97%) | 0.7 (99%) | 52.00 (0%) |
| Extraction 2 | 0.077 (97%) | 0.082 (97%) | ND (100%) | ND (100%) | ND (100%) | ND (100%) | 52.00 (0%) |
| Extraction 3 | ND (100%) | ND (100%) | ND (100%) | ND (100%) | ND (100%) | ND (100%) | 52.00 (0%) |
| Extraction 4 | ND (100%) | ND (100%) | ND (100%) | ND (100%) | ND (100%) | ND (100%) | 52.00 (0%) |
| Extraction with bis-(2-ethylhexyl) sebacate ($V_{aqueous}:V_{organic} = 2:1$) | | | | | | | |
| | | | | | | | TRS (g/L) |
| Standard | 2.723 | 2.956 | 565.9 | 565.9 | 300.2 | 485.6 | 52.00 |
| Extraction 1 | 0.595 (78%) | 0.620 (79%) | 35.2 (95%) | 38.6 (93%) | 20.1 (93%) | 12.2 (97%) | 52.00 (0%) |
| Extraction 2 | 0.097 (96%) | 0.106 (97%) | 16.3 (97%) | 16.3 (97%) | 2.3 (99%) | 1.5 (99%) | 52.00 (0%) |
| Extraction 3 | ND (100%) | ND (100%) | ND (100%) | ND (100%) | ND (100%) | ND (100%) | 52.00 (0%) |
| Extraction 4 | ND (100%) | ND (100%) | ND (100%) | ND (100%) | ND (100%) | ND (100%) | 52.00 (0%) |

*TRS = Total reducing sugar 1.11.2 Bio-Compatibility Study of Selected Organic-Solvents for Efficient Extraction of Microbial Inhibitors and Improved Bio-Butanol Production Bio-compatibility of the organic solvent used for extraction with solventogenic Clostridia is another important point to be considered, as ~5-10% of the organic compound could remain after phase separation. No data appears available regarding bis-(2-ethylhexyl) sebacate and 2-undecanone organic solvents' toxicity on Clostridia. In these cases, the octanol-water partition coefficient value (log $K_{OW}$) is usually cited as a toxicity parameter for the non-aqueous phase selection. Liquid organic solvent with log $K_{OW}$ values higher than 4 are generally considered as non-toxic for Gram-negative bacteria commonly found in off-gas treatment bioreactors (e.g. *Pseudomonas putida*) (Ramos et al. Mechanisms of solvent tolerance in gram-negative bacteria. Annual Reviews in Microbiology, Vol. 56(1), 2002: 743-768). However, species of the genus *Clostridium* are all Gram-positive.

In order to check the biocompatibility of these solvents considered for current investigation different sets of experiments as described in section 1.4 were subjected to batch fermentation. The results of the current investigation are presented in Table 5. When 52 g/L of glucose were provided to the $P_2$ medium without any inhibitor (set-1), about 12.85±0.2 g/L and 11.27±0.3 g/L of ABE were recorded for CA and CB strains after 72 h of fermentation with an average utilization of 35.3±1.2 g/L and 36.42±2.3 g/L of the available glucose respectively (Table 5). Set-2 and set-3 demonstrated that when (5-15%) of each solvent (2-undecanone and bis-(2-ethylhexyl) sebacate) were supplemented with set-1, bio-butanol generation in presence of 2-undecanone solvent was reduced by 70% and 67% for CA and CB respectively, in comparison with results obtained from set-1. However, bio-butanol production was remaining almost same with the control experiment upon same percentage of supplementation of bis-(2-ethylhexyl) sebacate as shown in Table 5. Thus, bio-compatibility experiments proved that bis-(2-ethylhexyl) sebacate was in fact more suitable for detoxification purposes as compared to 2-undecanone, in term of bio-butanol production. While 2-undecanone was retained as an alternative solvent, bis-(2-ethylhexyl) sebacate was preferred and considered for other investigation.

bio-butanol and ABE production did not reach the maximum values (set-1) probably also due to synergistic effects created between inhibitors, rather than the influence of each inhibitory compound concentration, as all the hydrolysis by-products were below their corresponding inhibition limit

TABLE 5

Bio-compatibility study of bis-(2-ethylhexyl) sebacate for efficient extraction of microbial inhibitors and improved bio-butanol production.

| N° Set | Composition | CA | | CB | |
|---|---|---|---|---|---|
| | | Butanol (g/L) | ABE (g/L) | Butanol (g/L) | ABE (g/L) |
| 1 | Control-1 52 g/L of glucose | 9.0 ± 0.5 | 12.85 ± 0.2 | 8.4 ± 0.5 | 11.27 ± 0.3 |
| 2 | Control-1 + (5-15)% 2-undecanone | 2.77 ± 0.12 | 3.82 ± 0.2 | 3.11 ± 0.3 | 4.28 ± 0.4 |
| 3 | Control-1 + (5-15)% bis-(2-ethylhexyl) sebacate | 9.13 ± 0.2 | 12.5 ± 0.2 | 8.62 ± 0.3 | 11.48 ± 0.4 |
| 4 | Control-2 52 g/L glucose + bacterial inhibitory solution (BIS) (3.0-3.2 g/L of both furfural and HMF; 0.5 g/L of the other compounds (vanillic acid, vanillin, syringaldehyde and ferulic acid)) | ND | ND | ND | ND |
| 5 | Control-3 (5 -15)% of each organic extractant without glucose and BIS | ND | ND | ND | ND |
| 6 | 52 g/L glucose + 5 times diluted BIS* | ND | ND | ND | ND |
| 7 | 52 g/L glucose + 10 times diluted BIS* | 2.1 ± 0.1 | 2.98 ± 0.4 | 1.1 ± 0.2 | 1.9 ± 0.3 |
| 8 | 52 g/L glucose + 50 times diluted BIS* | 7.12 ± 0.12 | 10.0 ± 0.2 | 6.13 ± 0.6 | 8.9 ± 0.3 |
| 9 | Control-2 + extraction (2:1 = agrowaste hydrolysate mimic: organic solvent) | 10.25 ± 0.5 | 13.96 ± 0.3 | 9.58 ± 0.2 | 13.15 ± 0.3 |
| 10 | Set-7 + extraction(2:1 = agro-waste hydrolysate mimic: organic solvent) | 9.13 ± 0.2 | 12.5 ± 0.2 | 8.62 ± 0.3 | 11.48 ± 0.4 |
| 11 | Set-8 + extraction(2:1 = agro-waste hydrolysate mimic: organic solvent) | 9.1 ± 0.3 | 12.2 ± 0.3 | 8.4 ± 0.2 | 11.0 ± 0.3 |

*BIS = bacterial inhibitory solution composed of 2.8-3.0 g/L of both furfural and HMF; 0.5 g/L of the other compounds (vanillic acid, vanillin, syringaldehyde and feluric acid). All the experiments were carried out in P2 nutrient Phenolic compounds, furan derivatives (furfural, 5-HMF) etc. have their detrimental effect in ABE fermentation depending on their concentration (Table 1). Phenolic compounds in waste hydrolysate, during ABE fermentation, interfere with the living cell by changing protein-to-lipid ratio in cell membrane and furan derivatives by utilizing NADH cofactor or NADPH for reduction instead of ABE production as shown in FIG. 1 (Jönsson et al. Bioconversion of lignocellulose: inhibitors and detoxification. Biotechnology for biofuels, Vol. 6(1), 2013:1). Thus, in order to check the effect of inhibition and detoxification using previously selected extracting solvent [bis-(2-ethylhexyl) sebacate], additional experiments were carried out and corresponding results were recorded in Table 5. About 9.5 g/L and 8.4 g/L of butanol production was observed from the control 1 conditions (52 g/L glucose) after 72 h of ABE fermentation (Table 5). Control 2 conditions [52 g/L glucose+bacterial inhibitory solution (BIS)] demonstrated that no production of butanol was achieved in any case (CA and CB) in the presence of typical toxic concentrations of each inhibitor (Table 1 & FIG. 1), corroborating the findings of (Baral et al., 2014).

Furthermore, to determine if the detrimental effect of inhibitory substrates was dose dependent, set-6, containing 52 g/L glucose+5× diluted BIS was subjected to fermentation and no desired metabolites were recorded for both cases. Thus, strong synergistic inhibitory effect below individual inhibitory level could be possible. Likewise, 10 times diluted BIS (set-7) solution resulted in (2.98±0.4) g/L and (1.9±0.3) g/L of ABE and production of bio-butanol increased up to 7.12±0.12 g/L for CA and 6.13±0.6 g/L for CB (31-32%!compared to control 1) when 50 times diluted inhibitor solution was used (set-8). In this dilution range, (Table 1). Thus, detoxification must be performed before fermentation to reduce the inhibitory effect due to presence of inhibitory substrates.

Production of butanol in set-9 after extraction of control 2 was higher than in previous experimental tests as it successfully removed the inhibitors from the fermentation broth. It was also evident that the production was even higher compared to control 1. Presence of lower concentration of furan derivative was reported to help in enhanced butanol production via a free, electron-mediated mechanism as shown in FIG. 1 (Baral et al., 2014). Thus, set-9 results suggested that the presence of furan derivatives traces in the media (incomplete removal as seen in Table 4) were utilized by the culture, and this might be the reason for improved yields in comparison with (control 1/set-1), achieving an average increase in the bio-butanol production (8-10)% for both bacterial strains. Experiments from set-10 and set-11 demonstrated that butanol productions were almost similar with the control 1 as the extraction process helped to remove (for both >99%) the inhibitors from the mimic synthetic media in this dilution range. Furthermore, control 3 (5-15% of each organic extractant without glucose and BIS) resulted in no butanol production which implied that the organic solvent was not utilized by CA and CB as a carbon source (in the presence or not of an additional easily assimilable carbon source like glucose), discarding its potential biodegradability. Thus, bis-(2-ethylhexyl) sebacate was chosen as the preferred solvent for removing microbial inhibitors from a real agro-industrial hydrolysate (BLW and BSG) as well as for optimizing further process operation parameters.

1.11.3 Brewery Industry Wastes and Physicochemical Characterization of Waste Biomass The physiochemical characterization of brewery industry spent grains (BSG) and brewery industry liquid waste (BLW) are presented in Table 3. In brewery industry after separation of wort, the residue left is called brewery spent grains (BSG) (Olajire, 2012; Macheiner et al. Pretreatment and hydrolysis of brewer's spent grains. Engineering in life sciences, Vol. 3(10), 2003: 401-405). Brewery industry liquid waste is a complex mixture of surplus yeast and plant residues (remaining fine particle BSG, spent hops), is semi-solid in nature, comes at the final stage after second fermentation, collected during tank wash (Fillaudeau et al., 2006, Olajire, 2012). Analysis of raw agro-industrial wastes revealed the presence of free reducing sugar in BLW: 15 g/L (10.5 g/L glucose, 2.5 g/L xylose) (Maiti et al., January 2016)

1.11.4 Enhanced Bio-Butanol Production Using BLW and BSG as Feedstock

Figure 2:
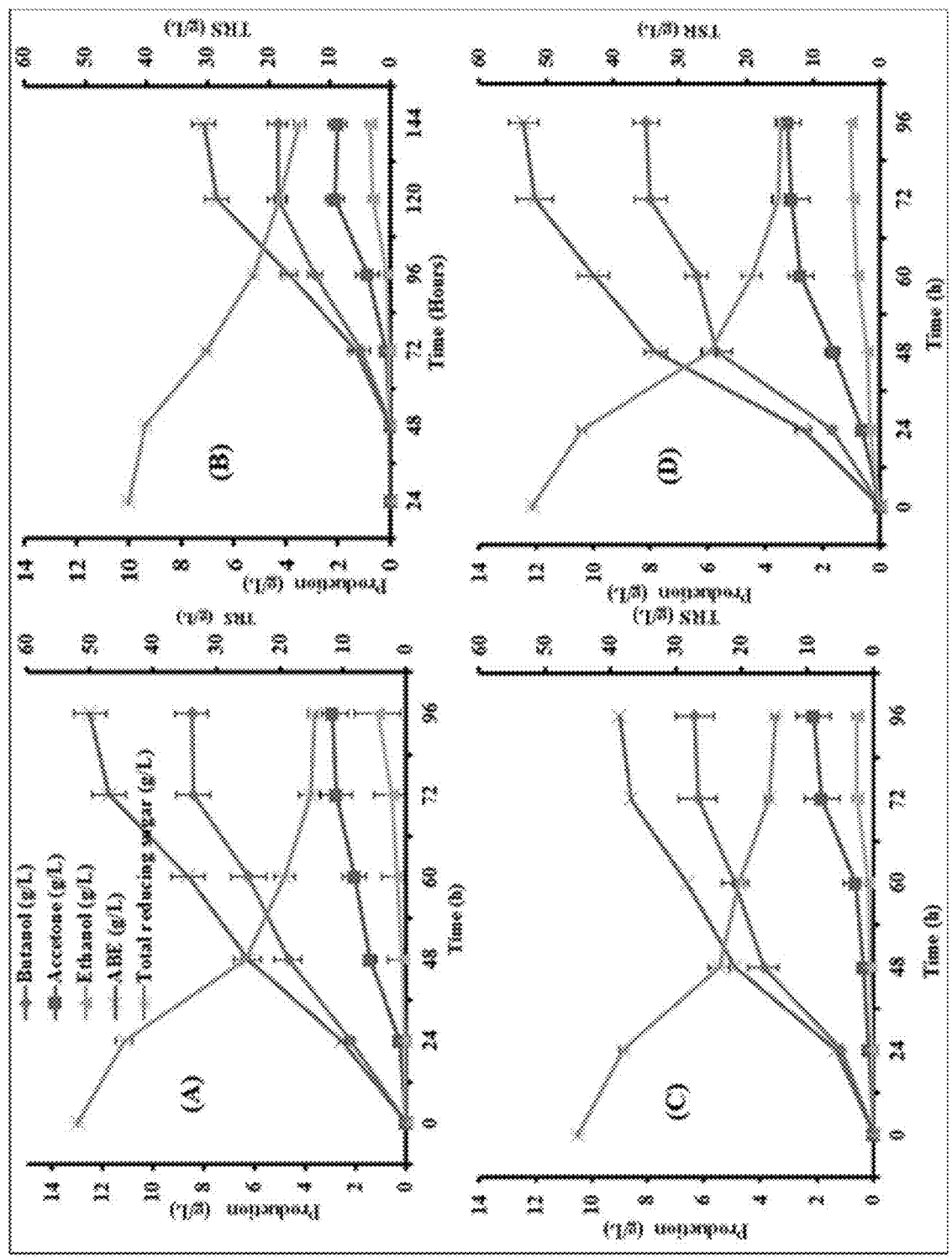
FIG. 2 shows graphs that illustrate the kinetics of metabolites production during ABE fermentation using brewery industry liquid waste (BLW): (A) control; (B) charcoal mediated detoxified BLW; (C) over-lime detoxified BLW; (D) two-phase partitioning bioreactor systems (TPPB) detoxified BLW.

Since one of the objectives of the present example is to utilize BLW and BSG hydrolysates as carbon sources to produce bio-butanol and improve bio-butanol production, un-hydrolyzed waste biomass were subjected to batch fermentation in $P_2$ media. Due to lack of sufficient reducing sugars no butanol production was observed like previously reported (Maiti et al., January 2016). In order to enhance butanol production, each biomass was subjected to hydrolysis. The resulting hydrolysates included sugars (TRS content of 52 g/L) and undesired microbial inhibitors as follows: furfural (0.642 g/L), HMF (3.123 g/L), levulinic acid (0.236 g/L) and total phenolic compounds (0.512) g/L in BLW hydrolysate and furfural (2.340 g/L), HMF (1.564 g/L) and total phenolic compounds (0.845 g/L) in BSG hydrolysate. Prior to detoxification, batch fermentation was run in $P_2$ media with both hydrolysates (TRS content of 52 g/L). As expected, the presence of different microbial inhibitors in the hydrolysate solutions (section 1.1) had strong synergistic effect on ABE fermentation inhibition and no bio-butanol production was attained. Accordingly, the two-phase extraction method of the present example and two previously known detoxification methods to enhance bio-butanol production from each hydrolysate were tested for comparison purposes as shown in Table 6.

for efficient conversion to ethanol as biofuel. Journal of Chemical Technology and Biotechnology, Vol. 91(6), 2016: 1826-1834). The currently developed detoxification method achieved an average increase of 46% and 25% in bio-butanol concentration in comparison with CaO overliming+ powdered activated charcoal and $Ca(OH)_2$ over-liming, respectively, from BLW. The kinetics of metabolites production using different detoxification method mediated ABE production using BLW has been presented in FIG. 2. FIG. 2: (A), (B), (C) and (D) presents the kinetics of metabolites formation from control, charcoal mediated detoxification followed by fermentation using BLW, overliming followed by fermentation and TPPB detoxification followed by fermentation using BLW respectively. Likewise, results obtained from BSG after fermentation was also recorded in Table 6. About 33% and 20% enhancement in butanol production was observed using the currently developed detoxification method compared to the other two (Table 6). The TRS loss observed with the known detoxification methods might be a main reason to explain this difference (Meinita et al., 2012). Additionally, these two methods were based on the conversion, to some extent, of the microbial inhibitors to their corresponding less toxic forms, unlike the currently developed method where all the phenolic compounds as well as soluble lignin were effectively extracted from the broth medium, ensuring no inhibition of the processes due to these compounds. Thus, *Clostridium beijerinckii* NRRL B-466 can successfully utilize the mixed free reducing sugars from the detoxified brewery industry waste hydrolysates to convert it into the desired products of ABE fermentation.

1.11.5 Translation of Flask Scale Data to Commercial-Scale TPPB Extraction

The transfer rate of the toxic compounds from the aqueous phase to the organic phase is proportional to the interfacial area, which itself is determined by the percentage of the organic solvent and the stirring conditions in the reactor. Once the identity and amount of a suitable organic solvent

TABLE 6

Bio-butanol production achieved by means of *Clostridium beijerinckii* after application of different detoxification methods.

| Substrates | CaO overliming + powdered activated charcoal | | $Ca(OH)_2$ overliming | | Two-phase extraction | |
|---|---|---|---|---|---|---|
| | Butanol (g/L) | Time (h) | Butanol (g/L) | Time (h) | Butanol (g/L) | Time (h) |
| BLW | 4.3 ± 0.3 | 120 | 6.2 ± 0.1 | 72 | 8.0 ± 0.12 | 72 |
| BSG | 4.8 ± 0.2 | 120 | 5.8 ± 0.3 | 72 | 7.2 ± 0.1 | 72 |

Figure 3:
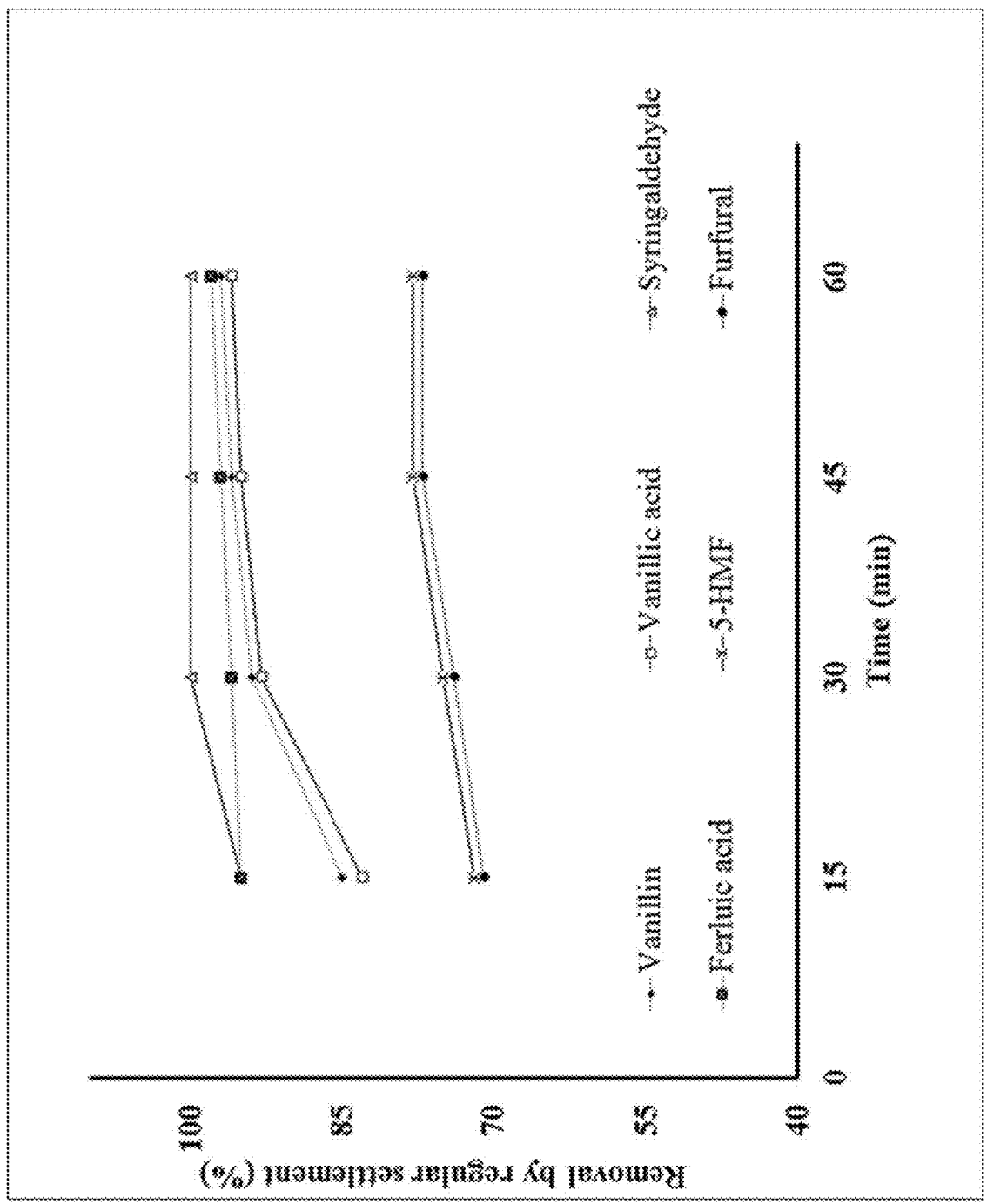
FIG. 3 is a graph that illustrates the effect of time during optimization of rotational speed of impeller propellant using 250 rpm.

A reduced bio-butanol production and productivity of charcoal mediated detoxification was observed compared to $Ca(OH)_2$ overliming and two-phase extraction method. Presence of suspended charcoal particles in the fermentation broth could be a reason for a longer lag-phase as shown in Table 6 and FIG. 2(B). In a similar way, Lopez-Linares et al. (2015) were not able to produce bio-ethanol or detect any consumption of glucose after 144 h when rape straw hydrolysate was detoxified by activated charcoal (López-Linares et al. Cofermentation of pentoses and hexoses by *Escherichia coli*. Spanish Journal of Agricultural Research, Vol. 13(3), 2015: 213). To a lesser extent, Gupta et al. (2015) observed a reduced bio-ethanol production rate for the first 2 h of fermentation when 2.0% ($wv^{-1}$) activated charcoal was used as detoxification method (Gupta et al. Scale-up of abatement of fermentation inhibitors from acid hydrolysates was determined, the stirring rate constituted the most important operational variable. Ascon-Cabrera and Lebeault (1995) found a fourfold linear increase in the interfacial area when increasing the agitation rate from 200 to 800 rpm (Ascon-Cabrera et al. Interfacial area effects of a biphasic aqueous/organic system on growth kinetic of xenobiotic-degrading microorganisms. Applied microbiology and biotechnology, Vol. 43(6), 1995: 1136-1141). However, agitation rates over 500 rpm were not recommended in a context of full-scale application due to the high energy consumptions and to the technical difficulties associated to their implementation (Gardin et al. Biodegradation of xylene and butyl acetate using an aqueous-silicon oil two-phase system. Biodegradation, Vol. 0(3), 1999: 193-200). In this example with increase in rotational speed from 100 to 250 rpm there was increase in extraction and no significant enhancements in microbial inhibitors extraction were observed with stirring rates above 250 rpm (Table 7). Centrifugal assisted separation performed equally well as a separating funnel, which nevertheless remains simpler and cheaper (Table 7). Furthermore, time is another important factor in this context. From FIG. 3, it is evident that using rotational speed 250 rpm, the extraction of different inhibitory compound were a lower after 15 min of extraction. However, when extraction time was increased to 30 minutes or more, the extraction levels were almost the same. Thus, rotational speed of 250 rpm and extraction time of 30 min appear to be suitable parameters.

TABLE 7

Optimization of different base line parameter to scale up

| Inhibitor | Phase separation by centrifugal force (%) Bi-phasic system homogenizer rotational speed (rpm) | | | | | Phase separation by separating funnel (%) Bi-phasic system homogenizer rotational speed (rpm) | | | | |
|---|---|---|---|---|---|---|---|---|---|---|
| | 100 | 200 | 250 | 300 | 400 | 100 | 200 | 250 | 300 | 400 |
| Furfural | 68 | 69 | 78 | 78 | 80 | 65 | 68 | 75 | 76 | 78 |
| HMF | 71 | 74 | 79 | 82 | 84 | 71 | 73 | 78 | 80 | 80 |
| Vanillin | 95 | 95 | 97 | 97 | 96 | 93 | 93 | 95 | 97 | 97 |
| Vanillic acid | 92 | 93 | 94 | 94 | 96 | 90 | 91 | 93 | 93 | 93 |
| Syringaldehyde | 100 | 100 | 100 | 100 | 100 | 100 | 100 | 100 | 100 | 100 |
| Ferulic acid | 97 | 96 | 97 | 95 | 97 | 94 | 94 | 93 | 94 | 96 |

The amount of power consumption is another determining factor to evaluate the suitability of the method proposed. In order to make a preliminary estimation of this value, the correlation proposed by Furukawa et al. (2012) for a propeller impeller in an unbaffled mixing vessel was applied taking into account several design parameters, such as liquid mixture viscosity, density and depth, vessel diameter, impeller diameter, angle and height of impeller blade, number of impeller blades, rotational speed and friction factor (Furukawa et al., 2012). Accordingly, the power consumption may be obtained by the following equation ($N_{po}$=Power Number):

$$P = N_{po} \times \text{bulk density} \cdot (\text{revolution per second})^3 \cdot (\text{impeller diameter})^5$$

The conditions used for the calculation of the power consumption were: an agitation speed of 250 rpm, an impeller diameter of 42 mm, a liquid mixture density of 955.15 kg/m$^3$ and a viscosity of 0.0091 Pa*s. Power inputs per unit volume for the reactor were therefore estimated to be 0.072 W/L, which can be considered a low value in comparison with other two-phase partitioning reactor cases described in the literature (Quijano et al. KLa measurement in two-phase partitioning bioreactors: new insights on potential errors at low power input. Journal of chemical technology and biotechnology, Vol. 85(10), 2010: 1407-1412).

1.12 Conclusion

In order to minimize environmental pollution and add positive momentum in bioenergy, carbon pool management of different brewery-industrial wastes such as brewery industry liquid waste (BLW) and spent grain (BSG) have been considered. An efficient, rapid ex-situ detoxification has been developed to reduce inhibitor concentration in the hydrolysate and enhance bio-butanol production. More than 80% extraction of furan derivatives and more than 95% extraction of phenolic compounds and almost no extraction of reducing sugar from simulated synthetic media as well as waste hydrolysate has made this method more interesting compared to literature reports. Ex-situ extraction of microbial inhibitors using bis-(2-ethylhexyl) sebacate as solvent leads to higher production of 8.0 g/L of bio-butanol from BLW compare to the use of literature reported methods such as over liming (6.2 g/L) and charcoal (4.3 g/L) detoxification. The currently developed detoxification method increased bio-butanol production potential of BLW because reasonable production of ABE was possible without sugar supplement. Extension of this solvent extraction detoxification method to BSG produced 7.2 g/L of bio-butanol. Lower power consumption and reuse of the extraction solvent make this detoxification technique useful for improved production of bio-butanol from agro-industrial waste hydrolysate.

Typically, in liquid-liquid extractions, the fermentation broth is extracted (in-situ or ex-situ) with a suitable hydrophobic, high boiling organic liquid to adsorb ABE, and the solvent unloaded broth is recycled to the fermenter. Bio-butanol is subsequently concentrated in a higher-boiling solvent and removed from the extractant in a recovery-regeneration unit (usually distillation), and the solvent is reused (Kraemer et al. Separation of butanol from acetone-butanol-ethanol fermentation by a hybrid extraction-distillation process. Computers & Chemical Engineering, Vol. 35(5), 2011: 949-963). In contrast, in the current case, the second phase is added in order to detoxify the hydrolysate before proceeding with the fermentation. Thus, maintaining an optimum and stable reuse efficiency of the organic solvent phase is even more important for commercial-scale extraction. As solvent extraction efficiency decreased in the range of 5-15% due to progressive saturation, organic liquid biological clean-up could be performed, so that the organic solvent would be reused without any energy intensive process. Phenolic compounds with similar characteristics to those found in lignocellulosic biomass hydrolysates have been previously efficiently degraded in two phase partitioning bioreactors (Table 8) developed for off-gases treatment by means of bacterial mixed cultures and specific strains.

TABLE 8

Biodegradation rates of different phenolic compounds typically found in off-gases by means of two-phase partitioning bio-reactors.

| Contaminant/Inhibitor | Bacteria | Solvent | Aqueous-organic phase ratio (v:v) | Concentration (mg/L) | Time to biodegrade (h) | Ref. |
|---|---|---|---|---|---|---|
| Styrene | Mixed culture wastewater plant | Silicone oil | 9:1 | 230 | 5 | (Dumont et al. Biotechniques for Air Pollution Control II, 2007) |
| 4-nitrophenol | Mixed culture wastewater plant | 2-undecanone | 9:1 | 350 | 7 | (Tomei et al. Water Science and Technology, 62(4), 2010) |
| Phenol | *Pseudomonas putida* ATCC 11172 | 2-undecanone | 2:1 | 4000 (168 in the aqueous phase) | 12 h lag-phase; Total consumption in 60 hours | (Collins et al. Biotechnology and bioengineering, 55(1), 1997) |
| Phenanthrene and pyrene | *Pseudomonas sp.* and *Sphingomonoas sp.* | Silicone oil | 2:1 | 100 | 72 h for phenanthrene; Pyrene was consumed as cosubstrate | (Guieysse et al.. Applied microbiology, 56(5-6), 2001) |
| Phenol (+ benzene + toluene) | *Pseudomonas putida* F1 | 2-undecanone | 16:1 | 400 | 28 | (Hamed et al. Biochemical Engineering Journal, 19(2), 2004) |
| Phenol | *Pseudomonas mandelii* | 2-Undecanone, diethyl sebacate | 3:1 | 4000-5000 | 24 h lag-phase, Total consumption in 75 h | (Guieysse et al. Water science and technology, 52(10-11), 2005) |
| Pentachlorophenol | *Sphingobiumchlorophenolicum* DSM 8671 | Dioctylsebacate | 2:1 | 10000-11000 | 60 h | (Zilouei et al. Chemosphere, 72(11), 2008) |

Example 2

Alternative Glycosidic Material

Brewery liquid waste (BLW), starch industry wastewater (SIW), and apple pomace ultrafiltration sludge (APUS) were pre-treated using diluted $H_2SO_4$ at 121±1° C. for 40 min to enhance total reducing sugar. Hydrolysates were kept overnight in 65° C. to raise the reducing sugar concentration, to around 60 g/L. The pH of the concentrated hydrolysate solution was adjusted to 10.5±0.1 by $Ca(OH)_2$ and was kept overnight at 40° C. to remove the excess metal ions as metal hydroxides and reduce the effect of process inhibitors. Hydroxide precipitate was centrifuged at 7650×g (10,000 rpm).

Prior to fermentation of agro-industrial wastes as well as hydrolysates, investigations were made for characterization of the complex agro-industrial waste biomass to assess carbohydrate pool and presence of micronutrients. The physiochemical characterization including total solids and free reducing sugars, carbohydrates, pH and micronutrients of three wastes, such as APUS, BLW and SIW were thoroughly investigated and is reported in Table 9. Analysis of raw agro-industrial wastes revealed the presence of free reducing sugar in BLW: 15 g/L (10.5 g/L glucose, 2.5 g/L xylose), APUS: 15 g/L (8 g/L glucose and 6.4 g/L fructose) and SIW (0.65 g/L).

TABLE 9

Chemical composition of waste biomass used for butanol production before and after hydrolysis

| Components | BLW | APUS | SIW | BLWH | APUSH | SIWH |
|---|---|---|---|---|---|---|
| pH | 5.4 ± 0.1 | 3.4 ± 0.1 | 3.3 ± 0.2 | — | — | — |
| Total Solid (g/L) | 129.4 ± 1.5 | 98.5 ± 2.4 | 15.9 ± 0.15 | — | — | — |
| Free reducing sugar (g/L) | 14.8 ± 1.4 | 13.0 ± 2.5 | 0.65 ± 0.15 | 30.0 ± 2.52 | 30.0 ± 2.68 | 30.0 ± 1.46 |
| Micronutrients (mg/L) (Element with wavelength) | | | | | | |
| Al (396.152) | 0.135 ± 0.01 | 0.66 ± 0.03 | 0.07 ± 0.01 | 0.05 ± 0.013 | 0.138 ± 0.02 | 0.01 ± 0.0 |
| As (188.980) | — | 0.06 ± 0.01 | — | — | 0.01 ± 0.02 | — |

TABLE 9-continued

Chemical composition of waste biomass used for butanol production before and after hydrolysis

| Components | BLW | APUS | SIW | BLWH | APUSH | SIWH |
|---|---|---|---|---|---|---|
| Ca (396.847) | 112.91 ± 2.5 | 104.36 ± 4.61 | 36.40 ± 3.5 | 7.6272 ± 1.72 | 5.93 ± 1.05 | 1.10 ± 0.54 |
| Co (238.892) | — | — | — | — | — | — |
| Cr (267.716) | 0.045 ± 0.02 | 0.145 ± 0.04 | 0.01 ± 0.0 | 0.02 ± 0.04 | 0.03 ± 0.02 | 0.02 ± 0.0 |
| Cu (324.754) | 0.43 ± 0.05 | 0.35 ± 0.05 | 0.08 ± 0.02 | 0.05 ± 0.06 | 0.01 ± 0.01 | 0.029 ± 0.01 |
| Fe (238.204) | 2.74 ± 0.43 | 29.086 ± 0.14 | 2.67 ± 0.05 | 0.05 ± 0.02 | 2.398 ± 0.05 | 0.09 ± 0.0 |
| K (769.897) | 785.36 ± 8.32 | 1332.69 ± 12.5 | 253.41 ± 6.28 | 714.315 ± 6.5 | 1298.78 ± 16.3 | 258.33 ± 4.2 |
| Mg (279.553) | 92.39 ± 2.54 | 67.78 ± 3.5 | 62.41 ± 2.48 | 32.37 ± 1.21 | 1.28 ± 0.04 | 0.198 ± 0.08 |
| Na (589.592) | 19.96 ± 1.71 | 554.94 ± 3.42 | 310.44 ± 5.62 | 1567.67 ± 12.5 | 1586.32 ± 5.81 | 1511.33 ± 25.6 |
| Ni (222.486) | 0.08 ± 0.01 | 0.06 ± 0.02 | 0.015 ± 0.03 | 0.042 ± 0.05 | 0.02 ± 0.01 | 0.01 ± 0.0 |
| P (213.618) | 461.14 ± 2.5 | 368.81 ± 3.51 | 124.28 ± 4.21 | 427.88 ± 1.21 | 240.77 ± 2.87 | 51.18 ± 2.5 |
| Pb (220.353) | — | — | — | — | — | — |
| S (181.972) | 179.26 ± 4.6 | 225.012 ± 1.63 | 79.13 ± 3.23 | 175.058 ± 4.31 | 149.44 ± 2.67 | 62.08 ± 5.8 |
| Se (196.026) | 0.10 ± 0.01 | 0.12 ± 0.05 | 0.07 ± 0.06 | 0.05 ± 0.02 | 0.05 ± 0.03 | 0.02 ± 0.0 |
| Zn (206.200) | 0.52 ± 0.01 | 0.45 ± 0.03 | 1.083 ± 0.02 | 0.02 ± 0.04 | 0.02 ± 0.02 | 0.05 ± 0.01 |

SIW: Starch Industry wastewater
APUS: Apple Pomace Ultrafiltration Sludge
BLW: Suspended Brewery Liquid Waste (BLW),
SIWH: Starch Industry Wastewater Hydrolysate
APUSH: Apple Pomace Ultrafiltration Sludge Hydrolysate
BLWH: Suspended Brewery Liquid Waste Hydrolysate It is important to note that in the present application, the microbial inhibitors are considered from the point of view of waste. However, it should be noted that these inhibitors are also for the most part molecules of interest having a good market value (ferulic acid, 200-300 $/kg, Vanillin 150 $/kg, etc.) and which could have applications other than that of being a simple waste. In fact, in some embodiments, if in one liter of hydrolysate there is 3 g/L of a furfural type inhibitor and 100 ml of solvent are added to recover it, one will effectively end up with this 3 g of furfural in 100 ml of solvent, which represents a 10-fold concentration. Therefore, another embodiment of the present invention may be the use of these solvents as extraction tools for phenolic compounds to concentrate the microbial inhibitors. Put another way, the target product are phenolic compounds and the waste would be the remaining sugars.

Example 3

Microwave Assisted Hydrolysis 3.1 Substrate Procurement and Preparation

The five agro-industrial residues (BLW, BSG, SIW, APS and APUS) selected for this example are nutrient-rich organic wastes generated in thousands of tones worldwide every year (Dhillon et al., 2011). Additionally, they have proven to be valid candidates for the production of higher value bio-products (Table 10). Three of the feedstock (BLW, SIW and APUS) were received as semi-solid substrates, while BSG and APS were in solid state. In order to compare their performance, all the biomasses were dried at 60° for 72 h prior to hydrolysis. The composition of the dry feedstocks is reported in Table 11.

TABLE 10 nutrient-rich organic wastes candidates for the production of higher value bio-products

| Feedstock | Biorefinery products |
|---|---|
| BLW | Substrate for microbial fuel cells |
|  | Bio-ethanol production |
| BSG | Nutraceuticals-rich solution production |
|  | Biogas production |
|  | Xylanase production |
| SIW | α-amylase and β-galactosidase production |
|  | Single-cell protein production with high lysine content |
|  | Lactic acid production |
| APS | Water soluble pigments production |
|  | Exo-pectinase production |
|  | Immobilization carrier for solid-state fermentation |
|  | Lacase production |
| APUS | Citric acid production |

TABLE 11

Physicochemical characterization of agro-industrial wastes.

| Components | BLW | BSG | APS | APUS | SIW |
|---|---|---|---|---|---|
| pH | 5.4 ± 0.1 | 5.2 ± 0.1 | 3.2 ± 0.1 | 3.4 ± 0.1 | 3.3 ± 0.2 |
| Total Solid (g/L) | 229.4 ± 1.5 | — | — | 384.5 ± 2.4 | 16.4 ± 0.15 |
| % Ash Content | 8.947 ± 1.34 | 7.785 ± 0.65 | 4.705 ± 0.53 | 2.549 ± 0.78 | 3.549 ± 0.94 |
| % Extractive | 5.733 ± 0.56 | 3.526 ± 0.42 | 3.115 ± 0.78 | 2.850 ± 0.23 | 1.243 ± 0.74 |
| Starch % (W/dry weight) | 5.6 ± 1.2 | 12.5 ± 0.85 | — | — | 30 ± 1.56 |
| Cellulose % (W/dry weight) | 19.8 ± 1.67 | 17.1 ± 0.97 | 23.2 ± 1.3 | 21.8 ± 1.78 | — |

TABLE 11-continued

Physicochemical characterization of agro-industrial wastes.

| Components | BLW | BSG | APS | APUS | SIW |
|---|---|---|---|---|---|
| Hemicellulose % (W/dry weight) | 16.5 ± 2.87 | 32.5 ± 1.45 | 5.4 ± 0.67 | — | — |
| Lignin (W/dry weight) | 8.5 ± 1.78 | 13.4 ± 1.9 | 23.5 ± 2.13 | 20.56 ± 2.56 | — |
| Free reducing sugar (g/kg) | 102.844 ± 4.67 | 22.660 ± 5.34 | 155.064 ± 2.12 | 175.360 ± 5.89 | 21.567 ± 0.98 |
| Glucose(g/kg) | 55.768 ± 1.34 | 1.567 ± 0.078 | 35.552 ± 0.98 | 40.345 ± 1.76 | 1.245 ± 0.09 |
| Fructose(g/kg) | — | — | 32.678 ± 1.67 | 30.678 ± 2.67 | — |
| Galactose(g/kg) | 5.946 ± 0.89 | — | 3.876 ± 0.67 | — | — |
| Xylose(g/kg) | 5.678 ± 0.92 | — | 3.145 ± 0.98 | — | — |
| Micronutrients(mg/kg) | | | | | |
| Cd (214.439) | 4.155 ± 0.65 | 7.315 ± 0.25 | — | — | 1.305 ± 0.05 |
| Al (308.215) | 8677.31 ± 105 | 1098.8 ± 135 | 653.24 ± 121 | 3905.985 ± 142 | 5678.9 ± 95 |
| Mn (257.610) | 1550.84 ± 112 | 4464.25 ± 145 | 2147.695 ± 139 | 1080.025 ± 89 | 6.4 ± 1.45 |
| Al (396.152) | 8914.725 ± 256 | 1450.06 ± 186 | 971.1 ± 126 | 4106.59 ± 155 | — |
| As (188.980) | 68.805 ± 5.04 | 13.88 ± 2.64 | 27.875 ± 3.67 | 34.08 ± 1.64 | 30.40 ± 1.24 |
| Ca (315.887) | 310588.5 ± 156 | 243347 ± 124 | 75017.45 ± 136 | 42284.8 ± 256 | 10950.6 ± 180 |
| Co (230.786) | 25.15 ± 0.23 | 2.655 ± 0.02 | 6.85 ± 0.86 | 4.825 ± 1.23 | 8.9 ± 2.04 |
| Cr (267.716) | 49.77 ± 1.56 | 55.59 ± 1.56 | 36.82 ± 1.56 | 131.245 ± 1.56 | 2.67 ± 1.56 |
| Cu (327.395) | 2125.56 ± 56.23 | 1119.57 ± 36.14 | 582.78 ± 156.67 | 471.185 ± 126.05 | 253.41 ± 112.28 |
| Fe (238.204) | 12077.45 ± 114 | 12068.8 ± 134 | 4326.76 ± 123 | 12652.3 ± 104 | 5341 ± 78.67 |
| K (766.491) | 95475.75 ± 88.56 | 52329.85 ± 75.06 | 27466.95 ± 64.56 | 44156.25 ± 198.04 | 26241 ± 108.56 |
| Mg (280.270) | 1877.84 ± 123 | 2095.73 ± 156 | 2769.27 ± 101 | 2752.28 ± 132 | 3104.4 ± 121.67 |
| Na (588.995) | 23141.1 ± 92 | 11154.2 ± 106.90 | 2662.86 ± 86.78 | 7835.53 ± 167.89 | 2141.5 ± 78.67 |
| Ni (222.486) | 263.67 ± 23.56 | 87.47 ± 3.78 | 101.53 ± 17.50 | 161.28 ± 20.65 | — |
| P(213.618) | 10532.95 ± 178 | 69458.75 ± 145 | 84583.65 ± 128 | 17234.4 ± 278 | — |
| Pb (220.353) | 4.66 ± 0.46 | 3.87 ± 1.23 | — | — | 7.5 ± 1.64 |
| Se (196.026) | 123.335 ± 12.23 | 100.435 ± 32.09 | 66.315 ± 10.20 | 46.1 ± 8.23 | 108 ± 22.11 |
| Zn (213.857) | 10526.6 ± 156.36 | 7311.895 ± 45.06 | 684.825 ± 66.30 | 239.93 ± 16.09 | 256.789 ± 23.16 |

3.2 Substrate Selection

The pre-screening process was developed by microwave-assisted Brønsted acid-catalysed hydrolysis at 161° C. for 25 minutes with a feedstock mass concentration of 40 g/L. The microwave (MARS™ microwave extractor, CEM Corporation, North Carolina, USA) was applied at 1000 W and hydrochloric acid (HCl) (2 N) was employed as homogeneous mineral acid solution. HCl (36.5-38 w/w %) was obtained from Fisher Scientific (USA). Each run was performed in triplicate. Reaction parameters were chosen as an approximate guide based on known examples of renewable lignocellulosic biomasses and agro-industrial wastes tested as raw materials for levulinic acid (LA) production as summarized in Table 12. Nevertheless, choice of hydrolysis treatment and its severity might differ hinging on the heterogeneity and complexity of the substrate (Morone et al. Levulinic acid production from renewable waste resources: bottlenecks, potential remedies, advancements and applications. Renewable and Sustainable Energy Reviews, Vol. 51, 2015: 548-565). The substrate(s) achieving a higher production of the sum of LA were used for further parameter optimisation by means of RSM for hyper-production of LA. Glucose and 5-HMF content was also going to be taken into account since they are starting molecules for LA synthesis via one-pot acid catalyst from lignocellulosic biomass.

TABLE 12

Hydrolysis reaction parameters for various substrates

| Substrate | Hydrolysis strategy | Acid (concentration) | Temp (K) | Time (min) | Substrate concentration | LA yield (%)* |
|---|---|---|---|---|---|---|
| Empty fruit bunch | Pretreatment: [EMIM][Cl] Brønsted acid catalyzed pressurized thermal hydrolysis | $H_2SO_4$ (8.1% wt) | 439 | 44.5 | 10% wt | 31.6 |
| Kenaf | Pretreatment: [EMIM][Cl] Brønsted acid catalyzed pressurized thermal hydrolysis | $H_2SO_4$ (7.8% wt) | 416 | 66.2 | 10% wt | 39.5 |
| Rice husk | Pretreatment: soxhlet extraction Brønsted acid catalyzed pressurized (56 bar) thermal hydrolysis | HCl (4.5% (v/v)) | 443 | 60 | 100 g/L | 59.4 |
| Cicer arietinum | Brønsted acid catalyzed pressurized thermal hydrolysis | HCl (1M) | 423 | 120 | 50 g/L | 32.6 |
| Pinus radiata | Brønsted acid catalyzed pressurized thermal hydrolysis | HCl (1M) | 423 | 120 | 50 g/L | 19.0 |
| Sugarcane bagasse | Brønsted acid catalyzed pressurized thermal hydrolysis | HCl (1M) | 423 | 120 | 50 g/L | 36.5 |
| Sugarcane bagasse | Brønsted acid catalyzed pressurized thermal hydrolysis | HCl (4.45% wt) | 493 | 45 | 10.5% wt | 22.8 |
| Paddy straw | Brønsted acid catalyzed pressurized thermal hydrolysis | HCl (4.45% wt) | 493 | 45 | 10.5% wt | 23.7 |
| Wheat straw | Brønsted acid catalyzed pressurized thermal hydrolysis | $H_2SO_4$ (3.5%) | 482 | 37.6 | 6% wt | 19.86 |
| Paper mill sludge | Brønsted acid catalysed, pressurized (30 bar, $N_2$) thermal hydrolysis | $H_2SO_4$ (98%) - 8.3 meq | 473 | 60 | 72.9 g/L | 15.4 |
| Corncob residue | Lewis acid catalyzed pressurized (20 bar, $N_2$) thermal hydrolysis; NaCl acted as promoter | 4:1 ($w_{corncob}$:$w_{AlCl_3}$) | 453 | 120 | 40 g/L | 20.9 |

TABLE 12-continued

Hydrolysis reaction parameters for various substrates

| Substrate | Hydrolysis strategy | Acid (concentration) | Temp (K) | Time (min) | Substrate concentration | LA yield (%)* |
|---|---|---|---|---|---|---|
| Post-harvest tomato plant waste | Microwave assisted (1000 W) flash pressurized (40 bar, $N_2$) thermal hydrolysis | HCl (1M) | 498 | 2 | 100 g/L | 63** |
| Wheat straw | Microwave-assisted (250 W) Brønsted acid-catalysed thermal hydrolysis | Betaine hydrochloride (40% wt) | 453*** | 60 | 1.3% wt | 23.1 |
| Chitin | Microwave-assisted (250 W) Brønsted acid-catalysed thermal hydrolysis | $H_2SO_4$ (2M) | 463 | 30 | 50 g/L | 21.6 |
| Poplar sawdust | Microwave-assisted (250 W) Brønsted acid catalyzed pressurized (30 bar, $N_2$) thermal hydrolysis | HCl (37%) - 11.5 meq | 473 | 15 | 72.9 g/L | 29.3 |
| Olive tree pruning | Microwave-assisted (250 W) Brønsted acid catalyzed pressurized (30 bar, $N_2$) thermal hydrolysis | HCl (37%) - 11.5 meq | 473 | 15 | 72.9 g/L | 20.1 |
| Chitosan | Microwave-assisted Lewis acid-catalysed thermal hydrolysis | $SnCl_4 \cdot 5H_2O$ (0.06M) | 473 | 30 | 25 g/L | 23.9 |

*Levulinic acid yield was defined as: "Yield of levulinic acid (wt %) = 100 × (levulinic acid after reaction (g))/(Initial biomass content (g))"
**Tabasso et al (2014) defined levulinic acid yield as: "Yield of levulinic acid (wt %) = 100 × (organic content in soluble fraction (g))/(Organic content in the biomass (g))"
***The reaction was first conducted at 150° C. to produce furfural and then at 180° C. to produce levulinic acid.

3.3 LA Production During Screening Study

During HCl catalysed thermo-hydrolysis, cellulose and hemicellulose are degraded into hexoses (e.g. glucose and fructose), the key intermediates in the production of LA. Hexoses are primarily dehydrated to 5-HMF, which is accelerate by Brønsted acid catalysts, and thereupon 5-HMF is rehydrated into LA with a theoretical yield of 64.5 wt % due to formic acid conjoint formation (Tarabanko et al. Sodium hydrosulfate as the catalyst for carbohydrate conversion into the levulinic acid and 5-hydroxymetylfurfural derivatives. Journal of Siberian Federal University, Vol. 1, 2008: 35-49). Pentoses produced via hemicellulose hydrolysis, such as xylose, can also be transformed in LA, but several separation steps are compulsory. This multi-process includes xylose dehydration to furfural, which is converted to furfuryl alcohol (via gas phase hydrogenation step) and finally to LA by means of a hydrolytic ring opening reaction (Hu et al. One-pot synthesis of levulinic acid/ester from C5 carbohydrates in a methanol medium. ACS Sustainable Chemistry Engineering, Vol. 1, 2013: 1593-1599).

LA production during the screening of the five agro-industrial residues is shown in Table 13. LA production of 204.4, 159.7, 66.4, 49.5 and 12.0 g/kg were recorded for BLW, BSG, APS, APUS and SIW, respectively. Accordingly, BSG and BLW were selected for further optimisation tests of reaction time, HCl concentration, and feedstock concentration making use of RSM for higher LA production. Both substrates exhibited the highest LA generation compared with the other feedstock. Moreover, they also contained some starch in their composition (Table 11), which is known to reach higher LA yields with milder treatment conditions in comparison to pure lignocellulosic biomasses (Morone et al, 2015). Owing to the content of TRS (especially glucose) and 5-HMF, LA production was expected to enhance with the improved parameters.

TABLE 13

Characterization of the hydrolysis products

| Feedstock | TRS (g/kg) | Glucose (g/kg) | Xylose (g/kg) | 5-HMF (g/kg) | Furfural (g/kg) | Levulinic acid (g/kg) |
|---|---|---|---|---|---|---|
| APS | 258.8 | 53.9 | 9.4 | 6.7 | 24.3 | 66.4 |
| APUS | 336.8 | 143.9 | Nd | 12.6 | 8.4 | 49.5 |
| BLW | 123.1 | 34.1 | Nd | 7.6 | 6.5 | 204.4 |
| SIW | 253.3 | 146.2 | Nd | 35.8 | 6.1 | 12.0 |
| BSG | 141.2 | 32.7 | Nd | 8.2 | 48.2 | 159.7 |

Xylose depletion was attributed to the presence of HCl, since Brønsted acids were recognised as relevant factor for the selective conversion of xylose into furfural (Chamnakid et al., 2014).

3.4 LA Production Enhancement Utilizing BSG and BLW as Substrates

Table 14 represents the results of central composite design which consist of experimental data for studying the effect of three independent variables (reaction time (A), acid concentration (B) and feedstock concentration (C)) on LA production from BSG and BLW samples. LA production ranged from about 38.2 g/kg to a maximum 341.1 g/kg for BSG residue, while it oscillated from 45.9 g/kg to 409.3 g/kg for BLW waste.

During beer production, three (bio)chemical reactions (mashing, boiling, fermentation and maturation) and other three solid-liquid separations (wort separation, wort clarification and rough beer clarification) are required, generating a large amount of solid residues (BSG) and wastewater (BLW), which management constitutes a relevant problem for the brewing industry (Fillaudeau et al., 2006). As shown in Table 14, the present example demonstrates the potential of BLW and BSG for high LA production (409 g/kg and 341 g/kg) by means of microwave-assisted HCl-catalysed thermal hydrolysis without prior special pretreatment, offering at the same time a solution to the prevailing environmental problem and a chance for balancing the books. A comparison with the results obtained by other authors using other alternative agro-industrial wastes and forestry residues (Table 12) place BLW and BSG in a highly ranked position.

Regarding the optimized parameters, the utilization of microwave heating allowed to halve the time process from >1 h to less than 30 min. Apart from process time reduction, heating method has not offered additional improvements (e.g. acid concentration reduction) in the literature (Szabolcs et al. Microwave-assisted conversion of carbohydrates to levulinic acid: an essential step in biomass conversion. Green Chemistry, Vol. 15, 2013). With respect to HCl concentration, LA production achieved a maximum at HCl 4.5 N for both substrates and then decreased rapidly with the further rise of the acid concentration. A substrate concentration of 85 g/L resulted in maximum LA production from BSG and BLW samples, which could be considered a high substrate concentration in comparison with substrate concentrations as compared to other samples, as shown in Table 12.

TABLE 14

Experimental design and the responses of BSG and BLW feedstock obtained for the 20 different experiments proposed

| Test | Factor 1 A: Time (min) | Factor 2 B: Acid concentration (N) | Factor 3 C: Substrate concentration (g/L) | Response 1 Levulinic acid from BSG (g/kg) | Response 2 Levulinic acid from BLW (g/kg) |
|---|---|---|---|---|---|
| 1 | 15.00 | 2.00 | 50.00 | 112.6 | 133.1 |
| 2 | 27.50 | 4.50 | 143.86 | 132.5 | 156.0 |
| 3 | 27.50 | 4.50 | 85.00 | 341.1 | 409.3 |
| 4 | 27.50 | 4.50 | 85.00 | 341.1 | 409.3 |
| 5 | 27.50 | 4.50 | 85.00 | 341.1 | 409.3 |
| 6 | 27.50 | 4.50 | 85.00 | 341.1 | 409.3 |
| 7 | 15.00 | 7.00 | 50.00 | 87.7 | 102.2 |
| 8 | 27.50 | 0.30 | 85.00 | 205.4 | 236.4 |
| 9 | 48.52 | 4.50 | 85.00 | 96.1 | 105.3 |
| 10 | 40.00 | 2.00 | 50.00 | 107.9 | 119.5 |
| 11 | 6.48 | 4.50 | 85.00 | 91.5 | 105.7 |
| 12 | 40.00 | 2.00 | 120.00 | 147.2 | 165.7 |
| 13 | 27.50 | 4.50 | 85.00 | 341.1 | 409.3 |
| 14 | 27.50 | 4.50 | 85.00 | 341.1 | 409.3 |
| 15 | 40.00 | 7.00 | 120.00 | 103.7 | 114.4 |
| 16 | 15.00 | 7.00 | 120.00 | 96.1 | 105.9 |
| 17 | 27.50 | 8.70 | 85.00 | 94.1 | 110.9 |
| 18 | 27.50 | 4.50 | 26.14 | 38.2 | 45.9 |
| 19 | 15.00 | 2.00 | 120.00 | 85.4 | 98.4 |
| 20 | 40.00 | 7.00 | 50.00 | 56.1 | 77.3 |

Example 4

Pretreatment of Waste Biomass

Brewery liquid waste (BLW), starch industry waste (SIW), and apple pomace ultrafiltration sludge (APS) were semi-solid in nature while brewery industry spent grains (BSG), apple pomace solid waste (APS) were solid. To compare the efficiency of the of different hydrolysis techniques to produce fermentable sugars and inhibitors, the dried weight of the all biomass was determined. All the biomass was dried at 60° C. for 72 h prior to hydrolysis.

4.1 Different Hydrolysis Techniques to Produce Fermentable Sugars

Dried waste biomass was pre-treated by using 11 different hydrolysis techniques:

(a) Chemical:

(1) Brønsted acid catalyzed using autoclave: 1 (M) $H_2SO_4$ at 121±1° C. for 40 minutes, 13 psi (89.6 kPa); (2) Alkali catalyzed using autoclave: 1 (N) NaOH at 121±1° C. for 40 minutes, 13 psi (89.6 kPa), (pH=10.0±0.1); (3) $H_2O_2$ catalyzed acid hydrolysis in autoclave: $H_2O_2$ (30 v/v, 0.05 mL) at 121±1° C. for 40 minutes, 13 psi (89.6 kPa), (pH=3-3.1 with $H_2SO_4$); Microwave assisted: (4) Brønsted acid catalyzed using microwave digester: 1 (M) $H_2SO_4$ at 121±1° C. for 25 minutes, 1000 W; (5) Alkali catalyzed using microwave digester: 1 (N) NaOH at 121±1° C. for 40 minutes, (pH=10.0±0.1), 1000 W (b) Nano Spray Drier Particle Catalyzed:

(6) Fe nano particles (NPs) catalyzed inert condition acidic (pH=3-3.1) at 121±1° C. for 40 minutes, 13 psi (89.6 kPa) in autoclave; (7) Ca NPs catalyzed inert condition alkaline (pH=10.0±0.1) at 121±1° C. for 40 minutes, 13 psi (89.6 kPa) in autoclave; (8) Both Ca and Fe NPs catalyzed inert at 121±1° C. for 40 minutes, 13 psi (89.6 kPa) in autoclave;

(c) Hydrothermal:

(9) Neutral pH at 121±1° C. for 40 minutes, 13 psi (89.6 kPa) in autoclave (10) Neutral pH at 121±1° C. for 25 minutes, 1000 W in microwave digester;

(d) Mechanical: (11) Ultra-Sonication.

Prior to carrying out agro-industrial waste hydrolysate (AWH) fermentation as sole substrate, investigations were made to perform characterization of the complex agro-industrial waste biomass to ascertain the ability of Clostridium beijerinckii B-466 to ferment representative sugars present in the AWH. The physicochemical characterization components which are really important for bio-butanol production have been thoroughly investigated and reported in Table 11 above for all the considered waste biomass. It can be seen that unlike BSG and SIW, APUS, APS and BLW are already enriched with free reducing sugars.

4.2 Comparisons of Different Hydrolysis Techniques in the Production of Fermentable Sugars and Fermentation Inhibitors from Different Agro-Industrial Wastes Different hydrolysis techniques such as chemical, hydrothermal, mechanical and nanoparticles catalyzed techniques have been explored to enhance the fermentable reducing sugars, and the results of a comparative study of reducing sugar producing efficiency of these different hydrolysis techniques from agro-industrial wastes are presented in Table 15.

4.3 Brewery Industry Wastes

In brewery industry after separation of wort, the residue left is called brewery spent grains (BSG) (Olajire, 2012; Macheiner et al., 2003). It contains on dry weight basis about (50-62) % polysaccharide (Table 11). Brewery industry liquid waste (BLW), which is semi-solid in nature, came at the final stage after second fermentation (Olajire, 2012). It is enriched with free reducing sugar and yeast proteins additional with higher polysaccharide content.

Depending on the process condition cellulose and hemicellulose have been degraded in different reducing sugars such as glucose, galactose, xylose etc. Due to their typical lignocellulosic composition where outer lignin entirely covers and bounds inner polysaccharides, acid catalyzed hydrolysis is more promising over other techniques employed, as shown in the results of Table 15. Solubilization of hemicellulose was favored in lower pH compared to higher, alkali catalyzed hydrolysis, as acid catalyzed hydrolysis facilitated the breakdown of glycosidic bonds. However, hydrothermal, NPs catalyzed and mechanical techniques were proved to be less efficient in hemicellulose rich biomass. Acid catalyzed hydrolysis significantly reduced recalcitrance of lignocellulosic biomass. Moreover, microwave assisted acid catalyzed and acid catalyzed-autoclave conditioned hydrolysis have been analyzed with different results. Same acid strength 1 N catalyzed hydrolysis in autoclave proved to be more promising than microwave assisted one due to less further conversion of polysaccharides to reducing sugars and to fermentation inhibitors as shown in Table 15, which presents the results of a comparative study of fermentation inhibitors production with different hydrolysis techniques applied to agro-industrial wastes.

4.4 Apple Industry Wastes

Both apple pomace solid (APS) and apple pomace ultrafiltration sludge (APUS) are rich sources of carbohydrates, minerals, vitamins and dietary fibers. These can be exploited for the production of biobutanol. Easily biodegradable, high organic load containing apple industry wastes are produced worldwide in huge amount and these wastes must be managed in a right way to avoid noxious environmental effects (Dhillon et al., 2013). However, unlike brewery industry wastes these wastes were enriched with fructose. As shown in Table 11, APS is mainly composed of cellulose as polysaccharide, with more aldohexose compared to aldopentose. There was no hemicellulose analyzed in APUS.

The degradation of cellulose is thermally accelerated and acid catalyzes chain scission mechanism (Hu et al., 2012). NPs catalyzed hydrolysis, which has been previously reported to be successful in hydrolysis of crystalline cellulose (Feng et al. Solid- and nano-catalysts pretreatment and hydrolysis techniques. Pretreatment Techniques for Biofuels and Biorefineries, Green Energy and Technology Series, Springer, 2013), was not effective here. Since the susceptibility of cellulose over different pH range has been reported to be different and more efficient in lower pH, thus acid catalyzed hydrolysis proved more promising over other methods. Microwave assisted hydrothermal method has also proved to be near as effective as acid catalyzed hydrolysis for total reducing sugar production as shown in Table 15. Moreover, as shown in Table 16, microwave assisted hydrothermal method has also proved to produce less fermentation inhibitors as compared with acid catalyzed hydrolysis.

4.5 Starch Industry Wastes

Starch, second largest compound produced by plant next to lignocellulose, is found in waste materials produced from the processing of plant raw materials (Jin et al. Utilisation of starch processing wastewater for production of microbial biomass protein and fungal α-amylase by *Aspergillus oryzae*. Bioresource technology, Vol. 66(3), 1998: 201-206; Rakshit. Utilization of starch industry wastes. Bioconversion of Waste Materials to Industrial Products, Springer, 1998). Unlike cellulose (β1-4 glycosidic linkage polysaccharide), the starch (α1-4 glycosidic linkage polysaccharide) is reported to be hydrolyzed very easily (Rakshit, 1998). The physicochemical characterization of starch industry waste (SIW) is shown in Table 11.

As compared to acid catalyzed methods, other hydrolysis methods proved to be less effective as shown in Table 15. However, microwave assisted acid catalyzed hydrolysis method proved to be more promising as compared to acid-autoclave hydrolysis method. Moreover, as shown in Table 16, except for alkali-autoclave hydrolysis method, all other hydrolysis methods generated a low concentration of inhibitors.

TABLE 15

Comparative study of fermentable reducing sugars producing efficiency of different hydrolysis techniques from agro-industrial wastes

| Hydrolysis Technique | Treatments | BLW (g/kg) | | | | BSG (g/kg) | | | | APS (g/kg) | | | APUS (g/kg) | | SIW (g/kg) | |
|---|---|---|---|---|---|---|---|---|---|---|---|---|---|---|---|---|
| | | TRS (g/kg) | Glucose (g/kg) | Galactose (g/kg) | Xylose (g/kg) | Total RS (g/kg) | Glucose (g/kg) | Xylose (g/kg) | Galactose (g/kg) | Total RS (g/kg) | Glucose (g/kg) | Xylose (g/kg) | Total RS (g/kg) | Glucose (g/kg) | Total RS (g/kg) | Glucose (g/kg) |
| Chemical treatments | Acid/autoclave | 375.122 | 197.502 | 148.502 | 19.536 | 468.214 | 175.562 | 128.112 | 52.945 | 375.122 | 94.502 | 19.536 | 611.011 | 185.218 | 329.906 | 196.973 |
| | Acid + H$_2$O$_2$/autoclave | 290.911 | 85.61 | 85.61 | 1.0412 | 53.895 | 2.328 | 0.3225 | 1.524 | 290.911 | 85.61 | 1.0412 | 378.490 | 190.868 | 56.0387 | 2.07 |
| | Alkali | 244.365 | 78.348 | 78.348 | 0.266 | 37.493 | 2.158 | ND | ND | 244.365 | 78.348 | 0.266 | 628.062 | 202.827 | 152.498 | 2.842 |
| | Acid + Microwave | 360.730 | 122.18 | 122.18 | ND | 413.400 | 146.91 | 97.45 | 26.789 | 360.730 | 122.18 | ND | 336.844 | 143.893 | 359.313 | 246.202 |
| | NaOH + Microwave | 199.657 | ND | ND | 1.12 | 59.866 | 2.475 | ND | ND | 199.657 | ND | 1.12 | 299.638 | 78.127 | 62.0100 | 1.901 |
| NPs catalyzed | CaNSPs | 255.389 | 1.603 | 1.603 | 0.522 | 122.182 | 10.428 | ND | ND | 255.389 | 1.603 | 0.522 | 335.234 | 56.235 | 171.790 | 3.318 |
| | (Fe + Ca) NSPs | 295.198 | 4.183 | 4.183 | 1.736 | 57.876 | 8.7175 | 1.965 | 0.078 | 295.298 | 4.183 | 1.736 | 353.651 | 63.503 | 264.576 | 17.733 |
| | FeNSPs | 131.981 | 7.79 | 7.79 | 0.233 | 36.134 | 0.681 | 0.1575 | ND | 131.981 | 7.79 | 0.233 | 256.567 | 43.671 | 138.259 | 2.253 |
| Mechanical | Ultra-sonication | 333.843 | 100.486 | 100.486 | ND | 180.567 | 22.545 | ND | ND | 333.843 | 100.486 | ND | 520.118 | 197.102 | 120.567 | 2.545 |
| Thermal | Neutral/Microwave | 404.519 | 104.532 | 104.532 | ND | 208.235 | 33.168 | ND | ND | 404.519 | 104.532 | ND | 631.277 | 186.781 | 128 | 3.168 |
| | Neutral/Microwave | 229.973 | 71.308 | 71.308 | 0.3575 | 32.469 | 0.658 | ND | ND | 229.973 | 71.308 | 0.3575 | 597.899 | 199.557 | 32.469 | 0.658 |

TABLE 16

Comparative study of fermentation inhibitors production with different hydrolysis techniques applied to agro-industrial wastes

| Hydrolysis Technique | Treatments | BLW (g/kg) | | | BSG (g/kg) | | | APS (g/kg) | | | APUS (g/kg) | | | SIW (g/kg) | | |
|---|---|---|---|---|---|---|---|---|---|---|---|---|---|---|---|---|
| | | 5-HMF | Furfural | Levulinic acid | 5-HMF | Furfural | Levulinic acid | 5-HMF | Furfural | Levulinic acid | 5-HMF | Furfural | Levulinic acid | 5-HMF | Furfural | Levulinic acid |
| Chemical treatments | Acid/autoclave | 21.346 | 1.65 | 9.525 | 3.17 | 11.45 | 2.75 | 45.501 | 3.125 | 13.85 | 37.575 | 1.263 | 19.25 | 2.689 | 1.561 | 0.007 |
| | Acid + $H_2O_2$/autoclave | 16.927 | 0.725 | 0.375 | 0.168 | 0.375 | 0.375 | 2.875 | 0.625 | 0.375 | 2.608 | 0.421 | 0.375 | ND | 0.725 | 0.198 |
| | Alkali | 0.145 | 0.375 | 0.375 | 0.218 | 0.375 | 0.375 | 0.312 | 0.375 | 0.375 | 0.92 | 2.825 | 0.375 | 120.401 | 3.240 | 12.290 |
| | Acid + Microwave | 29.736 | 1.780 | 4.008 | 13.589 | 48.592 | 2.921 | 17.41 | 4.601 | 0.375 | 0.307 | 0.20 | ND | 3.582 | 6.094 | 0.201 |
| | NaOH + Microwave | ND | 0.057 | 0.066 | 0.299 | 0.205 | 0.018 | 0 | 0.431 | 0.139 | 0 | 0.430 | 0.138 | ND | 0.162 | ND |
| NPs catalyzed | CaNSPs | ND | 0.081 | ND | 0.597 | 2.366 | 0.062 | 0.135 | <0.375 | 0.375 | 0.215 | <0.375 | <0.375 | ND | 1.062 | 0.285 |
| | (Fe + Ca) NSPs | 0.782 | 0.656 | ND | 0.695 | 0.475 | 0.375 | 0.147 | <0.375 | 0.95 | 0.354 | <0.375 | 0.45 | ND | 5.603 | ND |
| | FeNSPs | 0.491 | 0.375 | 0.375 | 0.3818 | 0.0482 | 0.0790 | 0.126 | <0.375 | 2.2 | <0.375 | <0.375 | 0.1345 | ND | 0.128 | ND |
| Mechanical | Ultra-sonication | ND | 0.239 | 0.375 | ND | 0.239 | 0.375 | ND | 0.089 | ND | 3.810 | 2.275 | 0.375 | ND | 0.239 | 0.019 |
| Thermal | Neutral/Microwave | ND | 0.259 | 0.375 | ND | 0.259 | 0.375 | 1.698 | 6.747 | ND | 12.445 | 1.246 | ND | ND | 0.259 | ND |
| | Neutral/Microwave | ND | ND | ND | ND | ND | ND | 0.312 | 0.375 | 0.375 | NF | 0.047 | ND | ND | ND | ND |

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. A process for extracting a microbial inhibitor from a hydrolysate of glycosidic waste matter containing free reducing sugars prior to a fermentation reaction, the process comprising the step of:
    solvent extraction of said hydrolysate with a solvent selected from the group consisting of bis-(2-ethylhexyl) sebacate, 2-undecanone, and a combination thereof, over a period of sufficient length to extract said microbial inhibitor therefrom, thereby obtaining an extract containing said microbial inhibitor and reducing the level of said microbial inhibitor in said hydrolysate.

2. A process for the production of bio-butanol by fermentation of a detoxified hydrolysate of glycosidic waste matter containing free reducing sugars, the process comprising the step of:
    fermentation of said detoxified hydrolysate with a solventogenic microorganism over a period of sufficient length and at a temperature sufficient to produce said bio-butanol,
    wherein said detoxified hydrolysate is obtained from a solvent extraction of a hydrolysate of glycosidic waste matter containing free reducing sugars with a solvent selected from the group consisting of bis-(2-ethylhexyl) sebacate, 2-undecanone, and a combination thereof, over a period of sufficient length to extract a microbial inhibitor therefrom, thereby obtaining an extract containing said microbial inhibitor and said detoxified hydrolysate.

3. The process of claim 2, further comprising the step of:
    solvent extraction of a hydrolysate of glycosidic waste matter containing free reducing sugars with a solvent selected from the group consisting of bis-(2-ethylhexyl) sebacate, 2-undecanone, and a combination thereof, over a period of sufficient length to extract a microbial inhibitor therefrom, thereby obtaining an extract containing said microbial inhibitor and said detoxified hydrolysate.

4. The process of claim 1, wherein said hydrolysate of glycosidic waste matter containing free reducing sugars is a hydrolysate of cellulosic waste matter containing free reducing sugars, a hydrolysate of amylosic waste matter containing free reducing sugars, or a combination thereof.

5. The process of claim 2, wherein said hydrolysate of glycosidic waste matter containing free reducing sugars is obtained from cellulosic waste matter, amylosic waste matter, or a combination thereof.

6. The process of claim 5, wherein said cellulosic waste matter is obtained from brewery liquid waste, brewery spent grain, apple pomace ultrafiltration sludge, apple pomace solid waste, or combinations thereof, and wherein said amylosic waste matter is from starch industry wastewater.

7. The process of claim 1, wherein said solvent is bis-(2-ethylhexyl) sebacate.

8. The process of claim 1, wherein a ratio of hydrolysate of glycosidic waste matter containing free reducing sugars to solvent ($v_{aqueous}:v_{organic}$) is from 5:1 to 1:2.

9. The process of claim 8, wherein said ratio is 2:1, or 5:1, or 3:1, or 1:1, or 1:2.

10. The process of claim 1, comprising mixing of said hydrolysate and said solvent during solvent extraction.

11. The process of claim 10, wherein mixing is performed by providing an input of energy from 0.02 to 0.12 W·h/L.

12. The process of claim 1, wherein said period of sufficient length to extract said microbial inhibitor is from 15 to 60 minutes.

13. The process of claim 1, wherein said solvent extraction is performed at a temperature from 15° C. to 30° C.

14. The process of claim 1, wherein said solvent extraction comprises separating said obtained hydrolysate from said solvent using at least one of a funnel separation, a centrifugal force-assisted separation, and a combination thereof.

15. The process of claim 1, wherein said obtained hydrolysate is produced by hydrolysis of glyosidic waste matter, said hydrolysis comprising at least one of a chemical hydrolysis, a thermal hydrolysis, an enzymatic hydrolysis, a mechanical hydrolysis, and combinations thereof.

16. The process of claim 15, wherein said obtained hydrolysate is produced by said thermal hydrolysis of said glycosidic waste matter, said thermal hydrolysis comprising at least one of a microwave-assisted hydrolysis and an autoclave-assisted hydrolysis.

17. The process of claim 2, wherein said fermentation is performed at a temperature from 30° C. to 40° C.

18. The process of claim 2, wherein said fermentation is performed in batch mode for at least 48 hours, or in batch mode for 72 hours.

19. The process of claim 2, wherein said solventogenic microorganism comprises a clostridia bacteria.

20. The process of claim 19, wherein said clostridia bacteria comprises at least one of *Clostridium acetobutylicum* NRRL B-582, *Clostridium beijerinckii* NRRL B-466 and a combination thereof.

* * * * *